(12) United States Patent
Wilson et al.

(10) Patent No.: US 11,555,206 B2
(45) Date of Patent: Jan. 17, 2023

(54) GENE THERAPY FOR MUCOPOLYSACCHARIDOSIS IIIA

(71) Applicant: The Trustees of the University of Pennsylvania, Philadelphia, PA (US)

(72) Inventors: James M. Wilson, Philadelphia, PA (US); Nathan Katz, Stamford, CT (US); Juliette Hordeaux, Philadelphia, PA (US)

(*) Notice: Subject to any disclaimer, the term of this patent is extended or adjusted under 35 U.S.C. 154(b) by 405 days.

(21) Appl. No.: 16/768,095

(22) PCT Filed: Nov. 29, 2018

(86) PCT No.: PCT/US2018/063168
§ 371 (c)(1),
(2) Date: May 29, 2020

(87) PCT Pub. No.: WO2019/108857
PCT Pub. Date: Jun. 6, 2019

(65) Prior Publication Data
US 2020/0291429 A1    Sep. 17, 2020

Related U.S. Application Data

(60) Provisional application No. 62/593,081, filed on Nov. 30, 2017.

(51) Int. Cl.
| | |
|---|---|
| *C12N 15/86* | (2006.01) |
| *A61P 19/00* | (2006.01) |
| *A61K 35/76* | (2015.01) |
| *A61K 48/00* | (2006.01) |
| *C12N 7/00* | (2006.01) |
| *C12N 9/14* | (2006.01) |

(52) U.S. Cl.
CPC .............. *C12N 15/86* (2013.01); *A61K 35/76* (2013.01); *A61K 48/005* (2013.01); *A61P 19/00* (2018.01); *C12N 7/00* (2013.01); *C12N 9/14* (2013.01); *C12Y 310/01001* (2013.01); *C12N 2750/14122* (2013.01); *C12N 2750/14143* (2013.01)

(58) Field of Classification Search
CPC .................................. C12N 15/86; C12N 9/14
See application file for complete search history.

(56) References Cited

U.S. PATENT DOCUMENTS

| | | | |
|---|---|---|---|
| 6,596,535 | B1 | 7/2003 | Carter |
| 7,125,717 | B2 | 10/2006 | Carter |
| 7,282,199 | B2 | 10/2007 | Gao et al. |
| 7,456,683 | B2 | 11/2008 | Takano et al. |
| 7,588,772 | B2 | 9/2009 | Kay et al. |
| 7,790,449 | B2 | 9/2010 | Gao et al. |
| 7,906,111 | B2 | 3/2011 | Wilson et al. |
| 8,927,514 | B2 | 1/2015 | Chatterjee et al. |
| 9,102,949 | B2 | 8/2015 | Gao et al. |
| 9,585,971 | B2 | 3/2017 | Deverman et al. |
| 9,623,120 | B2 | 4/2017 | Chatterjee et al. |
| 2007/0036760 | A1 | 2/2007 | Wilson et al. |
| 2009/0197338 | A1 | 8/2009 | Vandenberghe et al. |
| 2013/0039888 | A1 | 2/2013 | McCarty |
| 2013/0045186 | A1 | 2/2013 | Gao et al. |
| 2015/0079038 | A1 | 3/2015 | Deverman et al. |
| 2015/0104863 | A1 | 4/2015 | Tubert et al. |
| 2015/0349911 | A1 | 12/2015 | Otsubo |

FOREIGN PATENT DOCUMENTS

| | | |
|---|---|---|
| EP | 1310571 | 11/2002 |
| EP | 2492347 A1 | 4/2015 |
| WO | WO 96/09378 | 3/1996 |
| WO | WO 2003/042397 | 5/2003 |
| WO | WO 2005/033321 | 4/2005 |
| WO | WO 2006/110689 | 10/2006 |
| WO | WO 2010/053572 | 5/2010 |
| WO | WO 2011/126808 | 10/2011 |
| WO | WO 2012/170930 | 12/2012 |
| WO | WO 2013/182683 | 12/2013 |
| WO | WO 2016/049230 | 3/2016 |
| WO | WO 2017/136500 A1 | 8/2017 |
| WO | WO 2017/136533 | 8/2017 |
| WO | WO 2017/160360 A2 | 9/2017 |
| WO | WO 2018/160582 | 9/2018 |

OTHER PUBLICATIONS

Tardieu et al., Intracerebral gene therapy in children with mucopolysaccharidosis type IIB syndrome: an uncontrolled phase ½ clinical trial, The Lancet Neurology, vol. 16(9)712-720, Sep. 2017.

Andersen et al., Herpesvirus-mediated gene delivery into the rat brain: specificity and efficiency of the neuron-specific enolase promoter, Cellular and Molecular Neurobiology, vol. 13(5):503-15, Oct. 1993.

Arbuthnot et al., In vitro and in vivo hepatoma cell-specific expression of a gene transferred with an adenoviral vector, Human Gene Therapy, vol. 7(13):1503-14, Aug. 1996.

Aucoin et al., Production of adeno-associated viral vectors in insect cells using triple infection: optimization of baculovirus concentration ratios, Biotechnology and Bioengineering, vol. 95(6):1081-92, Dec. 2006.

(Continued)

*Primary Examiner* — Tekchand Saidha
(74) *Attorney, Agent, or Firm* — Colleen M. Schaller; Howson & Howson LLP

(57) ABSTRACT

Provided herein is a recombinant AAV (rAAV) comprising an AAV capsid and a vector genome packaged therein, wherein the vector genome comprises an AAV 5' inverted terminal repeat (ITR), an engineered nucleic acid sequence encoding a functional hSGSH, a regulatory sequence which direct expression of hSGSH in a target cell, and an AAV 3' ITR. Also provided is a pharmaceutical composition comprising a rAAV as described herein in a formulation buffer, and a method of treating a human subject diagnosed with MPS IIIA.

25 Claims, 10 Drawing Sheets

Specification includes a Sequence Listing.

(56) References Cited

OTHER PUBLICATIONS

Buller et al., Characterization of adenovirus-associated virus-induced polypeptides in KB cells, Journal Virology, vol. 25(1):331-8, Jan. 1978.
Coutinho et al., et al, Less Is More: Substrate Reduction Therapy for Lysosomal Storage Disorders, International Journal of Molecular Sciences, vol. 17(7):1065, Jul. 2016.
Defendi et al., Sanfilippo Syndrome (Mucopolysaccharidosis Type III) Medication, Medscape, Mar. 2014.
Delgadillo et al., Genistein supplementation in patients affected by Sanfiippo Disease, Journal of Inherit Metabolic Disease, vol. 34(5):1039-44, Oct. 2011.
Galibert et al., Latest developments in the large-scale production of adeno-associated virus vectors in insect cells toward the treatment of neuromuscular diseases, Journal of Invertebrate Pathology, vol. 107:S80-S93, Supplement, Jul. 2011.
Gao et al., Adeno-associated viruses undergo substantial evolution in primates during natural infections, Proceedings of the National Academy of Sciences in the United States of America, vol. 100(10):6081-6086, May 2003.
Grimm et al., Titration of AAV-2 particles via a novel capsid ELISA: packaging of genomes can limit production of recombinant AAV-2, Gene Therapy, vol. 6:1322-1330, Aug. 1999.
Gray et al., Optimizing Promoters for Recombinant Adeno-Associated Virus-Mediated Gene Expression in the Peripheral and Central Nervous System Using Self-Complementary Vectors, Human Gene Therapy, vol. 22(9):1143-1153, Sep. 2011.
Green and Sambrook, Molecular Cloning: A Laboratory Manual, Cold 20 Spring Harbor Press, Cold Spring Harbor, NY (2012).
Hinderer et al., Widespread gene transfer in the central nervous system of cynomolgus macaques following delivery of AAV9 into the cisterna magna, Mol Therapy Methods Clinical Development, vol. 1:14051, Dec. 2014.
Hopwood et al., Diagnosis of Sanfilippo type A syndrome by estimation of sulfamidase activity using a radio labelled tetrasaccharide substrate, Clinica Chimica Acta, vol. 123(3):241-25-, Aug. 1982.
De Ruijter et al., Genistein in Sanfilippo disease: a randomized controlled crossover trial, Annals of Neurology, vol. 71(1):110-120, Dec. 2011.
Karpova et al., A fluorimetric enzyme assay for the diagnosis of Sanfilippo disease type A (MPS IIIA), Journal of Inherited Metabolic Disease, vol. 19(3):278-85, Oct. 1996.
Kim et al., Involvement of cholesterol-rich lipid rafts in interleukin-6-induced neuroendocrine differentiation of LNCaP prostate cancer cells, Endocrinology, vol. 145(2):613-9, Feb. 2004.
Kim et al, Use of the human elongation factor 1 alpha promoter as a versatile and efficient expression system, Gene, vol. 91(2):217-23, Jul. 1990.
Kondratov et al Direct Head-to-Head Evaluation of Recombinant Adeno-associated Viral Vectors Manufactured in Human versus Insect Cells, Molecular Therapy, vol. 25(12):2661-2675, Dec. 2017.
Kotin, R., Large-scale recombinant adeno-associated virus production, Human Molecular Genetics, vol. 20(R1):R2-6, Apr. 2011.
Kugler et al., Human synapsin 1 gene promoter confers highly neuron-specific longterm transgene expression from an adenoviral vector in the adult rat brain depending on the transduced area, Gene Therapy, vol. 10(4):337-47, Feb. 2003.
Li et al., Production and Characterization of Novel Recombinant Adeno-Associated Virus Replicative-Form Genomes: A Eukaryotic Source of DNA for Gene Transfer, PLoS One, vol. 8(8):e69879, Aug. 2013.
Lock et al., Absolute determination of single-stranded and self-complementary adeno-associated viral vector genome titers by droplet digital PCR, Human Gene Therapy Methods, vol. 25(2):115-25, Apr. 2014.
Lock et al., Rapid, Simple, and Versatile Manufacturing of Recombinant Adeno-Associated Viral Vectors at Scale. Human Gene Therapy, vol. 21(10):1259-71, Oct. 2010.
McCarty et al, Self-complementary recombinant adeno-associated virus (scAAV) vectors promote efficient transduction independently of DNA synthesis, Gene Therapy, vol. 8(16):1248-1254, Aug. 2001.
Mietzsch et al., OneBac 2.0: Sf9 Cell Lines for Production of AAV1, AAV2, and AAV8 Vectors with Minimal Encapsidation of Foreign DNA, Human Gene Therapy Methods, vol. 28(1):15-22, Feb. 2017.
Miyatake et al., Transcriptional targeting of herpes simplex virus for cell-specific replication, Journal of Virology, vol. 71(7):5124-32, Jul. 1997.
Piccioli et al., Neuroantibodies: Molecular cloning of a monoclonal antibody against substance P for expression in the central nervous system, Proc. Natl. Acad. Sci. USA, vol. 88:5611-5, Jul. 1991.
Piccioli et al., Neuroantibodies: Ectopic Expression of a Recombinant Anti-Substance P Antibody in the Central Nervous System of Transgenic Mice, Neuron, Vo. 15:373-384, Aug. 1995.
Rashnonejad et al., Large-Scale Production of Adeno-Associated Viral Vector Serotype-9 Carrying the Human Survival Motor Neuron Gene, Molecular Biotechnology, vol. 58(1):30-6, Jan. 2016.
Rayaprolu et al, Comparative Analysis of Adeno-Associated Virus Capsid Stability and Dynamics, Journal of Virology, vol. 87(24):13150-13160, Dec. 2013.
Rose et al., Structural proteins of adenovirus-associated viruses, Journal of Virology, vol. 8(5):766-770, Oct. 1971.
Sandig et al., HBV-derived promoters direct liver-specific expression of an adenovirally transduced LDL receptor gene, Gene Therapy, vol. 3(11):1002-9, Nov. 1996.
Sommer et al., Quantification of adeno-associated virus particles and empty capsids by optical density measurement, Molecular Therapy, vol. 7(1)122-8, Jan. 2003.
Su et al., In Vitro and in Vivo mRNA Delivery Using Lipid-Enveloped pH-Responsive Polymer Nanoparticles, Molecular Pharmaceutics, vol. 8(3):774-787, Mar. 2011.
Tardieu et al., Intracerebral administration of adeno-associated viral vector serotype rh. 1 0 carrying human SGSH and SUMF 1 cDNAs in children with mucopolysaccharidosis type IIIA disease: results of a phase I/II trial, Human Gene Therapy, vol. 25(6):506-16, Jun. 2014.
Thakur, Production of Recombinant Adeno-associated viral vectors in yeast, Thesis presented to the Graduate School of the University of Florida, 2012.
Thompson et al., A comprehensive comparison of multiple sequence alignment programs, Nucleic Acid Research, vol. 27(13):2682-90, Jul. 1999.
Ugrinov et al., A Multiparametric Computational Algorithm for Comprehensive Assessment of Genetic Mutations in Mucopolysaccharidosis Type IIIA (Sanfilippo Syndrome), PLoS One, vol. 10(3):e0121511, Mar. 2015.
Whyte et al., Variables influencing fluorimetric N-sulfoglucosamine sulfohydrolase (SGSH) activity measurement in brain homogenates, Molecular Genetics and Metabolism Reports, vol. 5:60-62, Dec. 2015.
Wobus et al., Monoclonal antibodies against the adeno-associated virus type 2 (AAV-2) capsid: epitope mapping and identification of capsid domains involved in AAV-2-cell interaction and neutralization of AAV-2 infection, Journal Virology, vol. 74(19):9281-93, Oct. 2000.
Yampolsky et al. The Exchangeability of Amino Acids in Proteins, Genetics, vol. 170(4):1459-1472, Aug. 2005.
GenBank accession No. AAS99264.
GenBank accession No. AY530579.1.
International Search Report and Written Opinion issued in International Patent Application No. PCT/US2018/63168, dated Feb. 6, 2019.
Duncan et al., Broad functional correction of molecular impairments by systemic delivery of scAAVrh74-hSGSH gene delivery in MPS IIIA mice, Mol Ther. Apr. 2015;23(4):638-47.
Fraldi et al., Functional correction of CNS lesions in an MPS-IIIA mouse model by intracerebral AAV-mediated delivery of sulfamidase and SUMF1 genes, Hum Mol Genet. Nov. 15, 2007;16(22):2693-702.

(56) References Cited

OTHER PUBLICATIONS

Ruzo et al., Correction of pathological accumulation of glycosaminoglycans in central nervous system and peripheral tissues of MPSIIIA mice through systemic AAV9 gene transfer, Hum Gene Ther. Dec. 2012;23(12):1237-46.
Extended European Search Report and Written Opinion for European Patent Application No. 18884183.7, dated Nov. 3, 2021.

total GAG in Heart

FIG. 5

| | Fur Quality |
|---|---|
| 0 | Shiny coat, smooth fur, well groomed, clean coat |
| 1 | Not well groomed, slightly oily or rough coat |
| 2 | Rough Hair coat - haircoat is oily, dirty, stands on end |
| 3 | Very rough hair coat, dehydration |

| | Gait / Mobility |
|---|---|
| 0 | Active, energetic |
| 1 | Able to run, but sluggish |
| 2 | Reluctant to move, but will respond to prodding |
| 3 | Moves only when manually prodded & minimally |

| | Tremor |
|---|---|
| 0 | No sign of tremor |
| 1 | Very slight, impermanent |
| 2 | Mild, visible when compared to WT |
| 3 | Moderate, evident without comparison |
| 4 | Severe, impacts mobility |

| | Clasping |
|---|---|
| 0 | Legs splay out when lifted |
| 1 | 1 leg pulls in, not permanent |
| 2 | 1 leg permanently OR both legs impermanently pulled inward |
| 3 | 1 permanent and 1 impermanent leg pulled inward |
| 4 | Both legs pull in, permanent |

| | Posture |
|---|---|
| 0 | Normal, flat back |
| 1 | Transitory hunching, evident only when resting or lifted by tail only |
| 2 | Rests upright with back hunched, back stays hunched when moving |
| 3 | Almost always hunched |

| | Corneal Opacity |
|---|---|
| 0 | Clear Cornea |
| 1 | Slight Corneal Haze |
| 2 | Moderate Corneal Opacity |
| 3 | Severe Corneal Opacity - Iris visible |
| 4 | Severe Corneal Opacity - Iris not visible |

SEQUENCE LISTING

```
<160> NUMBER OF SEQ ID NOS: 7

<210> SEQ ID NO 1
<211> LENGTH: 1509
<212> TYPE: DNA
<213> ORGANISM: Artificial Sequence
<220> FEATURE:
<223> OTHER INFORMATION: Engineered nucleic acid sequence encoding human
      N-sulfoglycosamine sulfohydrolase (hSGSH)

<400> SEQUENCE: 1
atgagctgcc ctgtgcctgc ctgttgtgcc ctgctgctgg tgctgggact gtgcagagcc      60
agacccagaa acgctctgct gctgctggcc gacgatggcg gctttgagag cggcgcctac     120
aacaacagcg ccattgccac ccctcacctg gacgccctg ccagaagaag cctgctgttc      180
agaaacgcct tcaccagcgt gtccagctgc agccctagca gagcctctct gctgaccgga     240
ctgcctcagc accagaacgg gatgtacggc ctgcaccagg acgtgcacca cttcaacagc     300
ttcgacaaag tgcggagcct gccactgctg ctgtctcagg ctggcgtgcg gacaggcatc     360
atcggcaaga aacacgtggg cccgagaca gtgtacccct tcgacttcgc ctacaccgaa      420
gagaacggca gcgtgctgca agtgggccgg aacatcaccc ggatcaaact gctcgtgcgg     480
aagttcctgc agacccagga cgaccggcc ttcttcctgt acgtggcctt ccacgacccc      540
cacagatgtg gccactccca gcctcagtac ggcaccttct gcgagaagtt cggcaacggc     600
gagagcggca tgggcagaat ccctgattgg acccccagg cctacgaccc cctggatgtg     660
```

-continued

```
ctggtgccct acttcgtgcc aacacccct gccgccagag ccgatctggc cgcccagtat    720
acaaccgtgg gcaggatgga tcagggcgtg ggactggtgc tgcaggaact gagggacgcc    780
ggcgtgctga cgacaccct cgtgatcttt accagcgaca acggcatccc attccccagc    840
ggccggacca atctgtactg gcctggaaca gccgagcccc tgctggtgtc tagccctgag    900 cacccctaaga gatggggcca ggtgtccgag gcctacgtgt ccctgctgga tctgaccccc    960
accatcctgg actggttcag catcccctac cccagctacg ccatcttcgg ctccaagacc   1020
atccacctga ccggcagatc tctgctgcct gccctggaag ccgaacctct gtgggccaca   1080
gtgtttggca gccagagcca ccacgaagtg accatgtcct accccatgcg gagcgtgcag   1140
caccggcact tcagactggt gcacaacctg aacttcaaga tgcccttccc aatcgaccag   1200
gacttctatg tgtccccaac cttccaggac ctgctgaaca gaaccacagc cggccagcct   1260
accggctggt acaaggacct gcggcactac tactaccggg ccagatggga gctgtacgac   1320
agaagcaggg accccacga gacacagaac ctggccaccg accctagatt cgcccagctg   1380
ctggaaatgc tgcgggacca gctggccaag tggcagtggg agacacacga cccttgggtg   1440
tgcgctcctg acggggtgct ggaagagaag ctgagccctc agtgccagcc cctgcacaac   1500
gagctgtga                                                           1509
```

<210> SEQ ID NO 2
<211> LENGTH: 502
<212> TYPE: PRT
<213> ORGANISM: Homo sapiens

<400> SEQUENCE: 2

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Ala Asp Asp
        20                  25                  30

Gly Gly Phe Glu Ser Gly Ala Tyr Asn Asn Ser Ala Ile Ala Thr Pro
    35                  40                  45

His Leu Asp Ala Leu Ala Arg Arg Ser Leu Leu Phe Arg Asn Ala Phe
50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
```

```
                 210                 215                 220
Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 3
<211> LENGTH: 1509
<212> TYPE: DNA
<213> ORGANISM: Homo sapiens

<400> SEQUENCE: 3
atgagctgcc ccgtgcccgc ctgctgcgcg ctgctgctag tcctgggggct ctgccgggcg      60 cgtccccgga acgcactgct gctcctcgcg gatgacggag ctttgagag tggcgcgtac     120 aacaacagcg ccatcgccac cccgcacctg gacgccttgg cccgccgcag cctcctcttt     180
cgcaatgcct tcacctcggt cagcagctgc tctcccagcc gcgccagcct cctcactggc     240
ctgccccagc atcagaatgg gatgtacggg ctgcaccagg acgtgcacca cttcaactcc     300
ttcgacaagg tgcggagcct gcgctgctg ctcagccaag ctggtgtgcg cacaggcatc     360
atcgggaaga agcacgtggg gccggagacc gtgtaccgt ttgactttgc gtacacggag     420
gagaatggct ccgtcctcca ggtggggcgg aacatcacta gaattaagct gctcgtccgg     480
```

```
aaattcctgc agactcagga tgaccggcct ttcttcctct acgtcgcctt ccacgacccc    540
caccgctgtg ggcactccca gccccagtac ggaaccttct gtgagaagtt tggcaacgga    600
gagagcggca tgggtcgtat cccagactgg acccccagg cctacgaccc actggacgtg     660
ctggtgcctt acttcgtccc caacaccccg gcagcccgag ccgacctggc cgctcagtac    720
accaccgtcg gccgcatgga ccaaggagtt ggactggtgc tccaggagct gcgtgacgcc    780
ggtgtcctga cgacacact ggtgatcttc acgtccgaca cgggatccc cttccccagc      840 ggcaggacca acctgtactg gccgggcact gctgaaccct tactggtgtc atccccggag    900
cacccaaaac gctggggcca agtcagcgag gcctacgtga gcctcctaga cctcacgccc    960
accatcttgg attggttctc gatcccgtac cccagctacg ccatctttgg ctcgaagacc   1020
atccacctca ctggccggtc cctcctgccg gcgctggagg ccgagcccct ctgggccacc   1080
gtctttggca gccagagcca ccacgaggtc accatgtcct accccatgcg ctccgtgcag   1140
caccggcact ccgcctcgt gcacaacctc aacttcaaga tgcccttttcc catcgaccag   1200 gacttctacg tctcacccac cttccaggac ctcctgaacc gcaccacagc tggtcagccc   1260
acgggctggt acaaggacct ccgtcattac tactaccggg cgcgctggga gctctacgac   1320
cggagccggg accccacga gacccagaac ctggccaccg acccgcgctt tgctcagctt   1380
ctggagatgc ttcgggacca gctggccaag tggcagtggg agaccacga cccctgggtg    1440 tgcgccccg acggcgtcct ggaggagaag ctctctcccc agtgccagcc cctccacaat    1500
gagctgtga                                                            1509

<210> SEQ ID NO 4
<211> LENGTH: 3837
<212> TYPE: DNA
<213> ORGANISM: Artificial Sequence
<220> FEATURE:
<223> OTHER INFORMATION: rAAV vector genome AAV.CB7.CI.hSGSHco.rBG
<220> FEATURE:
<221> NAME/KEY: repeat_region
<222> LOCATION: (1)..(130)
<223> OTHER INFORMATION: AAV2 5'ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(863)
<223> OTHER INFORMATION: CB promoter
<220> FEATURE:
<221> NAME/KEY: TATA_signal
<222> LOCATION: (836)..(839)
<220> FEATURE:
<221> NAME/KEY: Intron
<222> LOCATION: (958)..(1930)
<223> OTHER INFORMATION: chicken beta-actin
<220> FEATURE:
<221> NAME/KEY: CDS
<222> LOCATION: (1948)..(3459)
<223> OTHER INFORMATION: Engineered nucleic acid sequence encoding human
     N-sulfoglycosamine sulfohydrolase (hSGSH)
<220> FEATURE:
<221> NAME/KEY: polyA_signal
<222> LOCATION: (3493)..(3619)
<223> OTHER INFORMATION: Rabbit globin poly A (rBG, RBG)
<220> FEATURE:
<221> NAME/KEY: repeat_region
<222> LOCATION: (3708)..(3837)
<223> OTHER INFORMATION: AAV2 3'ITR

<400> SEQUENCE: 4
```

-continued

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctaccag ggtaatgggg | 180 |
| atcctctaga actatagcta gtcgacattg attattgact agttattaat agtaatcaat | 240 |
| tacggggtca ttagttcata gcccatatat ggagttccgc gttacataac ttacggtaaa | 300 |
| tggcccgcct ggctgaccgc ccaacgaccc ccgcccattg acgtcaataa tgacgtatgt | 360 |
| tcccatagta acgccaatag ggactttcca ttgacgtcaa tgggtggact atttacggta | 420 |
| aactgcccac ttggcagtac atcaagtgta tcatatgcca agtacgcccc ctattgacgt | 480 |
| caatgacggt aaatggcccg cctggcatta tgcccagtac atgaccttat gggactttcc | 540 |
| tacttggcag tacatctacg tattagtcat cgctattacc atggtcgagg tgagccccac | 600 |
| gttctgcttc actctcccca tctccccccc ctccccaccc ccaattttgt atttatttat | 660 |
| tttttaatta ttttgtgcag cgatggggc ggggggggg ggggggcgcg cgccaggcgg | 720 |
| ggcggggcgg ggcgaggggc ggggcgggc gaggcggaga ggtgcggcgg cagccaatca | 780 |
| gagcggcgcg ctccgaaagt ttccttttat ggcgaggcgg cggcggcggc ggccctataa | 840 |
| aaagcgaagc gcgcggcggg cggggagtcg ctgcgacgct gccttcgccc cgtgccccgc | 900 |
| tccgccgccg cctcgcgccg cccgcccgg ctctgactga ccgcgttact cccacaggtg | 960 |
| agcgggcggg acggcccttc tcctccgggc tgtaattagc gcttggttta atgacgcgct | 1020 |
| gtttcttttc tgtggctgcg tgaaagcctt gaggggctcc gggagggccc tttgtgcggg | 1080 |
| gggagcggct cggggggtgc gtgcgtgtgt gtgtgcgtgg ggagcgccgc gtgcggctcc | 1140 |
| gcgctgcccg gcggctgtga gcgctgcggg cgcggcgcgg ggctttgtgc gctccgcagt | 1200 |
| gtgcgcgagg ggagcgcggc cggggcggt gccccgcggt gcgggggggg ctgcgagggg | 1260 |
| aacaaaggct gcgtgcgggg tgtgtgcgtg ggggggtgag caggggtgt gggcgcgtcg | 1320 |
| gtcgggctgc aaccccccct gcaccccct ccccgagttg ctgagcacgg cccggcttcg | 1380 |
| ggtgcgggc tccgtacggg gcgtggcgcg gggctcgccg tgccgggcgg ggggtggcgg | 1440 |
| caggtgggg tgccgggcgg ggcggggccg cctcggcccg gggagggctc ggggagggg | 1500 |
| cgcggcggcc cccggagcgc cggcggctgt cgaggcgcgg cgagccgcag ccattgcctt | 1560 |
| ttatggtaat cgtgcgagag ggcgcaggga cttcctttgt cccaaatctg tgcggagccg | 1620 |
| aaatctggga ggcgccgccg caccccctct agcgggcgcg gggcgaagcg gtgcggcgcc | 1680 |
| ggcaggaagg aaatgggcgg ggagggcctt cgtgcgtcgc cgcgccgccg tccccttctc | 1740 |
| cctctccagc ctcggggctg tccgcggggg gacggctgcc ttcgggggg acggggcagg | 1800 |
| gcggggttcg gcttctggcg tgtgaccggc ggctctagag cctctgctaa ccatgttcat | 1860 |
| gccttcttct ttttcctaca gctcctgggc aacgtgctgg ttattgtgct gtctcatcat | 1920 |
| tttggcaaag aattcacgcg tgccacc atg agc tgc cct gtg cct gcc tgt tgt | 1974 |
|                                            Met Ser Cys Pro Val Pro Ala Cys Cys <br>                                            1                5 | |
| gcc ctg ctg ctg gtg ctg gga ctg tgc aga gcc aga ccc aga aac gct <br>Ala Leu Leu Leu Val Leu Gly Leu Cys Arg Ala Arg Pro Arg Asn Ala <br>10                 15                20                   25 | 2022 |
| ctg ctg ctg ctg gcc gac gat ggc ggc ttt gag agc ggc gcc tac aac <br>Leu Leu Leu Leu Ala Asp Asp Gly Gly Phe Glu Ser Gly Ala Tyr Asn <br>                 30                   35                   40 | 2070 |
| aac agc gcc att gcc acc cct cac ctg gac gcc ctg gcc aga aga agc <br>Asn Ser Ala Ile Ala Thr Pro His Leu Asp Ala Leu Ala Arg Arg Ser <br>           45                   50                   55 | 2118 |

-continued

| | |
|---|---|
| ctg ctg ttc aga aac gcc ttc acc agc gtg tcc agc tgc agc cct agc<br>Leu Leu Phe Arg Asn Ala Phe Thr Ser Val Ser Ser Cys Ser Pro Ser<br>        60                      65                 70 | 2166 |
| aga gcc tct ctg ctg acc gga ctg cct cag cac cag aac ggg atg tac<br>Arg Ala Ser Leu Leu Thr Gly Leu Pro Gln His Gln Asn Gly Met Tyr<br>75                     80                     85 | 2214 |
| ggc ctg cac cag gac gtg cac cac ttc aac agc ttc gac aaa gtg cgg<br>Gly Leu His Gln Asp Val His His Phe Asn Ser Phe Asp Lys Val Arg<br>90                     95                100           105 | 2262 |
| agc ctg cca ctg ctg ctg tct cag gct ggc gtg cgg aca ggc atc atc<br>Ser Leu Pro Leu Leu Leu Ser Gln Ala Gly Val Arg Thr Gly Ile Ile<br>            110                  115               120 | 2310 |
| ggc aag aaa cac gtg ggc ccc gag aca gtg tac ccc ttc gac ttc gcc<br>Gly Lys Lys His Val Gly Pro Glu Thr Val Tyr Pro Phe Asp Phe Ala<br>125                    130                135 | 2358 |
| tac acc gaa gag aac ggc agc gtg ctg caa gtg ggc cgg aac atc acc<br>Tyr Thr Glu Glu Asn Gly Ser Val Leu Gln Val Gly Arg Asn Ile Thr<br>        140                  145                150 | 2406 |
| cgg atc aaa ctg ctc gtg cgg aag ttc ctg cag acc cag gac gac cgg<br>Arg Ile Lys Leu Leu Val Arg Lys Phe Leu Gln Thr Gln Asp Asp Arg<br>155                    160                165 | 2454 |
| ccc ttc ttc ctg tac gtg gcc ttc cac gac ccc cac aga tgt ggc cac<br>Pro Phe Phe Leu Tyr Val Ala Phe His Asp Pro His Arg Cys Gly His<br>170                175                180                185 | 2502 |
| tcc cag cct cag tac ggc acc ttc tgc gag aag ttc ggc aac ggc gag<br>Ser Gln Pro Gln Tyr Gly Thr Phe Cys Glu Lys Phe Gly Asn Gly Glu<br>                  190                195                200 | 2550 |
| agc ggc atg ggc aga atc cct gat tgg acc ccc cag gcc tac gac ccc<br>Ser Gly Met Gly Arg Ile Pro Asp Trp Thr Pro Gln Ala Tyr Asp Pro<br>205                    210                215 | 2598 |
| ctg gat gtg ctg gtg ccc tac ttc gtg ccc aac acc cct gcc gcc aga<br>Leu Asp Val Leu Val Pro Tyr Phe Val Pro Asn Thr Pro Ala Ala Arg<br>        220                  225                230 | 2646 |
| gcc gat ctg gcc gcc cag tat aca acc gtg ggc agg atg gat cag ggc<br>Ala Asp Leu Ala Ala Gln Tyr Thr Thr Val Gly Arg Met Asp Gln Gly<br>235                    240                245 | 2694 |
| gtg gga ctg gtg ctg cag gaa ctg agg gac gcc ggc gtg ctg aac gac<br>Val Gly Leu Val Leu Gln Glu Leu Arg Asp Ala Gly Val Leu Asn Asp<br>250                    255                260                265 | 2742 |
| acc ctc gtg atc ttt acc agc gac aac ggc atc cca ttc ccc agc ggc<br>Thr Leu Val Ile Phe Thr Ser Asp Asn Gly Ile Pro Phe Pro Ser Gly<br>                  270                275                280 | 2790 |
| cgg acc aat ctg tac tgg cct gga aca gcc gag ccc ctg ctg gtg tct<br>Arg Thr Asn Leu Tyr Trp Pro Gly Thr Ala Glu Pro Leu Leu Val Ser<br>              285                290                295 | 2838 |
| agc cct gag cac cct aag aga tgg ggc cag gtg tcc gag gcc tac gtg<br>Ser Pro Glu His Pro Lys Arg Trp Gly Gln Val Ser Glu Ala Tyr Val<br>300                    305                310 | 2886 |
| tcc ctg ctg gat ctg acc ccc acc atc ctg gac tgg ttc agc atc ccc<br>Ser Leu Leu Asp Leu Thr Pro Thr Ile Leu Asp Trp Phe Ser Ile Pro<br>            315                  320                325 | 2934 |
| tac ccc agc tac gcc atc ttc ggc tcc aag acc atc cac ctg acc ggc<br>Tyr Pro Ser Tyr Ala Ile Phe Gly Ser Lys Thr Ile His Leu Thr Gly<br>330                    335                340                345 | 2982 |
| aga tct ctg ctg cct gcc ctg gaa gcc gaa cct ctg tgg gcc aca gtg<br>Arg Ser Leu Leu Pro Ala Leu Glu Ala Glu Pro Leu Trp Ala Thr Val<br>                350                355                360 | 3030 |
| ttt ggc agc cag agc cac cac gaa gtg acc atg tcc tac ccc atg cgg<br>Phe Gly Ser Gln Ser His His Glu Val Thr Met Ser Tyr Pro Met Arg | 3078 |

```
                       365                 370                 375
agc gtg cag cac cgg cac ttc aga ctg gtg cac aac ctg aac ttc aag         3126
Ser Val Gln His Arg His Phe Arg Leu Val His Asn Leu Asn Phe Lys
        380                 385                 390 atg ccc ttc cca atc gac cag gac ttc tat gtg tcc cca acc ttc cag         3174
Met Pro Phe Pro Ile Asp Gln Asp Phe Tyr Val Ser Pro Thr Phe Gln
395                 400                 405 gac ctg ctg aac aga acc aca gcc ggc cag cct acc ggc tgg tac aag         3222
Asp Leu Leu Asn Arg Thr Thr Ala Gly Gln Pro Thr Gly Trp Tyr Lys
410                 415                 420                 425 gac ctg cgg cac tac tac tac cgg gcc aga tgg gag ctg tac gac aga         3270
Asp Leu Arg His Tyr Tyr Tyr Arg Ala Arg Trp Glu Leu Tyr Asp Arg
            430                 435                 440 agc agg gac ccc cac gag aca cag aac ctg gcc acc gac cct aga ttc         3318
Ser Arg Asp Pro His Glu Thr Gln Asn Leu Ala Thr Asp Pro Arg Phe
                445                 450                 455 gcc cag ctg ctg gaa atg ctg cgg gac cag ctg gcc aag tgg cag tgg         3366
Ala Gln Leu Leu Glu Met Leu Arg Asp Gln Leu Ala Lys Trp Gln Trp
                    460                 465                 470 gag aca cac gac cct tgg gtg tgc gct cct gac ggg gtg ctg gaa gag         3414
Glu Thr His Asp Pro Trp Val Cys Ala Pro Asp Gly Val Leu Glu Glu
475                 480                 485 aag ctg agc cct cag tgc cag ccc ctg cac aac gag ctg tga tga             3459
Lys Leu Ser Pro Gln Cys Gln Pro Leu His Asn Glu Leu
490                 495                 500 ctcgaggacg gggtgaacta cgcctgagga tccgatcttt ttccctctgc caaaaattat       3519
ggggacatca tgaagcccct tgagcatctg acttctggct aataaaggaa atttattttc       3579
attgcaatag tgtgttggaa ttttttgtgt ctctcactcg gaagcaattc gttgatctga       3639
atttcgacca cccataatac ccattaccct ggtagataag tagcatggcg ggttaatcat       3699
taactacaag gaaccctag tgatggagtt ggccactccc tctctgcgcg ctcgctcgct        3759
cactgaggcc gggcgaccaa aggtcgcccg acgcccgggc tttgcccggg cggcctcagt       3819
gagcgagcga gcgcgcag                                                     3837

<210> SEQ ID NO 5
<211> LENGTH: 502
<212> TYPE: PRT
<213> ORGANISM: Artificial Sequence
<220> FEATURE:
<223> OTHER INFORMATION: Synthetic Construct

<400> SEQUENCE: 5

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
                100                 105                 110
```

Gln Ala Gly Val Arg Thr Gly Ile Ile Gly Lys Lys His Val Gly Pro
            115                 120                 125

Glu Thr Val Tyr Pro Phe Asp Phe Ala Tyr Thr Glu Glu Asn Gly Ser
130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
            195                 200                 205

Asp Trp Thr Pro Gln Ala Tyr Asp Pro Leu Asp Val Leu Val Pro Tyr
            210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
        290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 6
<211> LENGTH: 736
<212> TYPE: PRT

<213> ORGANISM: Artificial Sequence
<220> FEATURE:
<223> OTHER INFORMATION: capsid protein VP1 of adeno-associated virus 9

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

```
                385                 390                 395                 400
Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 2211
<212> TYPE: DNA
<213> ORGANISM: Artificial Sequence
<220> FEATURE:
<223> OTHER INFORMATION: nucleic acid sequence encoding capsid protein
      VP1 of adeno-associated virus 9

<400> SEQUENCE: 7
atggctgccg atggttatct tccagattgg ctcgaggaca accttagtga aggaattcgc     60
gagtggtggg ctttgaaacc tggagcccct caacccaagg caaatcaaca acatcaagac    120
```

-continued

```
aacgctcgag gtcttgtgct tccgggttac aaataccttg gacccggcaa cggactcgac      180 aaggggagc cggtcaacgc agcagacgcg gcggccctcg agcacgacaa ggcctacgac        240
cagcagctca aggccggaga caacccgtac ctcaagtaca accacgccga cgccgagttc      300
caggagcggc tcaaagaaga tacgtctttt ggggcaacc tcgggcgagc agtcttccag       360
gccaaaaaga ggcttcttga acctcttggt ctggttgagg aagcggctaa gacggctcct      420
ggaaagaaga ggcctgtaga gcagtctcct caggaaccgg actcctccgc gggtattggc      480
aaatcgggtg cacagcccgc taaaaagaga ctcaatttcg gtcagactgg cgacacagag      540
tcagtcccag accctcaacc aatcggagaa cctcccgcag cccctcagg tgtgggatct       600 cttacaatgg cttcaggtgg tggcgcacca gtggcagaca ataacgaagg tgccgatgga      660
gtgggtagtt cctcgggaaa ttggcattgc gattcccaat ggctggggga cagagtcatc     720
accaccagca cccgaacctg ggccctgccc acctacaaca atcacctcta caagcaaatc      780
tccaacagca catctggagg atcttcaaat gacaacgcct acttcggcta cagcaccccc     840
tgggggtatt ttgacttcaa cagattccac tgccacttct caccacgtga ctggcagcga      900
ctcatcaaca caactggggg attccggcct aagcgactca acttcaagct cttcaacatt     960
caggtcaaag aggttacgga caacaatgga gtcaagacca tcgccaataa ccttaccagc     1020
acggtccagg tcttcacgga ctcagactat cagctcccgt acgtgctcgg gtcggctcac    1080
gagggctgcc tcccgccgtt cccagcggac gtttttcatga ttcctcagta cgggtatctg   1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaagga gaggaccgtt tctttccttt gtctggatct     1620 ttaattttg gcaaacaagg aactggaaga gacaacgtgg atgcggacaa agtcatgata    1680
accaacgaag aagaaattaa aactactaac ccggtagcaa cggagtccta tggacaagtg   1740
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg   1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag   2100
tacacttcca actattacaa gtctaataat gttgaatttg ctgttaatac tgaaggtgta    2160
tatagtgaac cccgccccat tggcaccaga tacctgactc gtaatctgta a             2211
```

GENE THERAPY FOR MUCOPOLYSACCHARIDOSIS IIIA

CROSS-REFERENCE TO RELATED APPLICATIONS

This is a National Stage Entry under 35 U.S.C. 371 of International Patent Application No. PCT/US2018/063168, filed Nov. 29, 2018, which claims benefits to U.S. Provisional Patent Application No. 62/593,081, filed Nov. 30, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "18-8476PCT_ST25.txt".

BACKGROUND OF THE INVENTION

Mucopolysaccharidosis type IIIa (MPS IIIa, MPS IIIA, or Sanfilippo syndrome type A), is an autosomal recessive inherited disorder caused by the deficiency of the enzyme N-sulfoglycosamine sulfohydrolase (SGSH), involved in the lysosomal catabolism of the glycosaminoglycans (GAG) heparan sulfate. This deficiency leads to the intracellular accumulation of undegraded heparan sulfate as well as gangliosides GM2 and GM3 in the central nervous system causing neuronal dysfunction and neuroinflammation. The disease manifests first as a cognitive delay around 3 years of age followed by abnormal hyperactive and aggressive behavior. The progression of the disease then leads to a loss of motor and neurological functions during the first decade with death at a median age of 15 years.

There is currently no cure or standard treatment for people with MPS IIIA. Medications are used to relieve symptoms (such as anticonvulsants for seizures) and improve quality of life. Hematopoietic stem cell transplantation does not seem to ameliorate neuropsychological deterioration significantly. Recombinant enzymes for the deficiencies in MPS III are available, but trials in enzyme replacement therapy (ERT) have not been favorable in improving prognosis because the enzymes are not able to enter the central nervous system. See, e.g., Germaine L Defendi. Genetics of Mucopolysaccharidosis Type III. Medscape. Mar. 21, 2014. Changes to the diet do not prevent disease progression, but limiting milk, sugar, and dairy products has helped some people who have excessive mucus.

A continuing need in the art exists for compositions and methods for efficient treatment of MPS IIIA.

SUMMARY OF THE INVENTION

In one aspect, provided is a vector comprising an engineered nucleic acid sequence encoding a functional human N-sulfoglycosamine sulfohydrolase (hSGSH) and a regulatory sequence which direct expression thereof in a target cell. In one embodiment, the hSGSH coding sequence is at least 96% identical to SEQ ID NO: 1. In a further embodiment, the hSGSH coding sequence is SEQ ID NO: 1.

In another aspect, a recombinant AAV (rAAV) comprising an AAV capsid and a vector genome packaged therein is provided, wherein the vector genome comprises an AAV 5' inverted terminal repeat (ITR), an engineered nucleic acid sequence encoding a functional hSGSH, a regulatory sequence which direct expression of hSGSH in a target cell, and an AAV 3' ITR. In one embodiment, the hSGSH coding sequence is at least 95% identical to SEQ ID NO: 1. In a further embodiment, the AAV vector genome comprises the sequence of SEQ ID NO: 4 (AAV.CB7.CI.hSGSHco.RBG). In some embodiments, the AAV capsid is an AAV9 capsid. In one embodiment, the rAAV (AAV9.CB7.CI.hSGSHco.RBG) comprises an AAV9 capsid and a vector genome comprising the sequence of SEQ ID NO: 4.

Further provided is a pharmaceutical composition comprising a rAAV as described herein in a formulation buffer.

In yet another aspect, provided herein is a method of treating a human subject diagnosed with MPS IIIA, comprising administering to the subject a suspension of a rAAV as described herein in a formulation buffer.

In a further aspect, an expression cassette comprising an engineered nucleic acid sequence encoding a functional hSGSH, and a regulatory sequence which direct expression thereof is provided. In one embodiment, the hSGSH coding sequence in the expression cassette is at least 96% identical to SEQ ID NO: 1.

Other aspects and advantages of the invention will be readily apparent from the following detailed description of the invention.

BRIEF DESCRIPTION OF THE DRAWINGS

FIG. 5 provides a grading scale used to assess the clinical health of mice used in the studies to determine long-term effects of AAV9.CB7.CI.hSGSH.rBG treatment.

DETAILED DESCRIPTION OF THE INVENTION

Figure 1A:
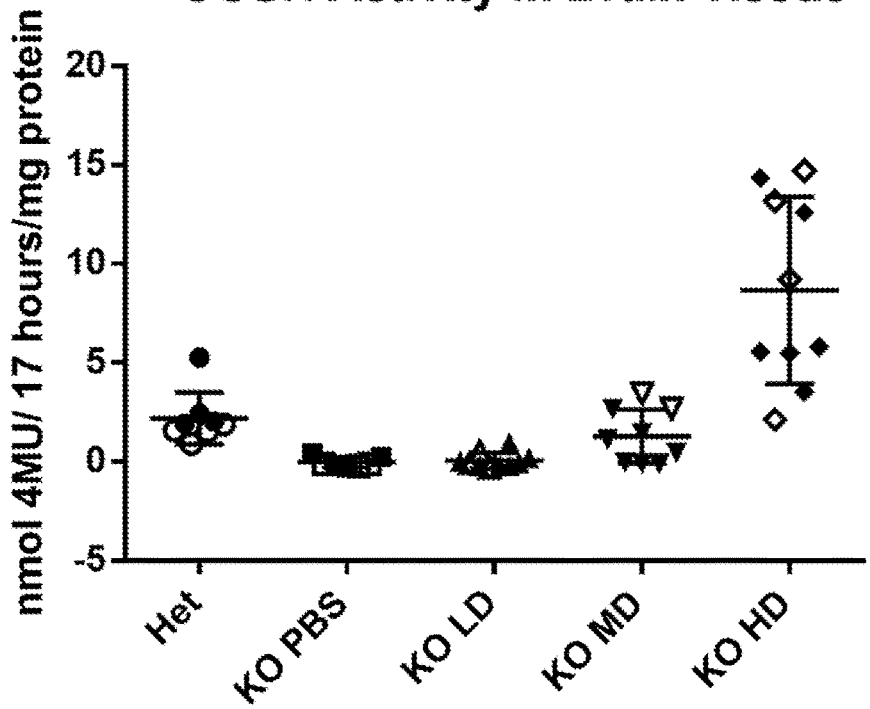
FIGS. 1A to 1E provide SGSH activity in brain (FIG. 1A), spinal cord (FIG. 1B), liver (FIG. 1C), and total GAG storage in heart (FIG. 1D) and brain (FIG. 1E) 6 months after intracerebroventricular administration of AAV9.CB7.CI.hSGSH.rBG. A dose dependent increase in SGSH activity was observed in the brain, spinal cord, and liver. Total GAGs were reduced in the heart at the high dose only. GAGs were increased in the brain of KO MPS IIIA mice and normalized at the mid- (MD) and high-dose (HD) by the treatment. Open symbols represent males while solid ones represent female in FIGS. 1A to 1C. LD refers to low-dose.

Compositions useful for the treatment of Mucopolysaccharidosis type IIIa (MPS IIIA) and/or alleviating symptoms of MPSIIIA are provided herein. These compositions comprise a nucleic acid sequence encoding a functional human N-sulfoglycosamine sulfohydrolase (hSGSH) and a regulatory sequence which direct expression thereof in a target cell, wherein the hSGSH coding sequence is at least 96% identical to SEQ ID NO: 1.

In one embodiment, the compositions and methods described herein involve nucleic acid sequences, expression cassettes, vectors, recombinant viruses, other compositions and methods for expression of a functional human SGSH. In another embodiment, the compositions and methods described herein involve nucleic acid sequences, expression cassettes, vectors, recombinant viruses, host cells, other compositions and methods for production of a composition comprising the nucleic acid sequence encoding a functional human SGSH. In yet another embodiment, the compositions and methods described herein involve nucleic acid sequences, expression cassettes, vectors, recombinant viruses, other compositions and methods for delivery of the nucleic acid sequence encoding a functional human SGSH to a subject for the treatment of MPS IIIA. In one embodiment, the compositions and methods described herein are useful for providing a therapeutic level of SGSH into the central nervous system (CNS). Additionally or alternatively, the compositions and methods described herein are useful for providing therapeutic levels of SGSH in the periphery, such as, e.g., blood, liver, kidney, or peripheral nervous system. In certain embodiments, an adeno-associated viral (AAV) vector-based method described herein provides a new treatment option, helping to restore a desired function of SGSH, to alleviate a symptom associated with MPS IIIA, to improve MPS IIIA-related biomarkers, or to facilitate other treatment(s) for MPS IIIA, by providing expression of SGSH protein in a subject in need.

As used herein, the term "a therapeutic level" means an enzyme activity at least about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, about 100%, more than 100%, about 2-fold, about 3-fold, or about 5-fold of a healthy control. Suitable assays for measuring SGSH enzymatic activity are described herein. In some embodiments, such therapeutic levels of SGSH may result in alleviation of the MPS III-A related symptoms; improvement of MPS IIIA-related biomarkers of disease; or facilitation of other treatment(s) for MPS IIIA, e.g., GAG levels in the cerebrospinal fluid (CSF), serum, urine and/or other biological samples; prevention of neurocognitive decline; reversal of certain MPS IIIA-related symptoms and/or prevention of progression of MPS IIIA-related certain symptoms; or any combination thereof.

As used herein, "a healthy control" refers to a subject or a biological sample therefrom, wherein the subject does not have an MPS disorder. The healthy control can be from one subject. In another embodiment, the healthy control is a pool of multiple subjects.

As used herein, the term "biological sample" refers to any cell, biological fluid or tissue. Suitable samples for use in this invention may include, without limitation, whole blood, leukocytes, fibroblasts, serum, urine, plasma, saliva, bone marrow, cerebrospinal fluid, amniotic fluid, and skin cells. Such samples may further be diluted with saline, buffer or a physiologically acceptable diluent. Alternatively, such samples are concentrated by conventional means.

With regard to the description of these inventions, it is intended that each of the compositions herein described, is useful, in another embodiment, in the methods of the invention. In addition, it is also intended that each of the compositions herein described as useful in the methods, is, in another embodiment, itself an embodiment of the invention.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

As used herein, "disease", "disorder" and "condition" are Mucopolysaccharidosis type IIIa (MPS IIIA, MPS IIIa, also known as Sanfilippo syndrome type A or Sanfilippo type A disease).

As used herein, the term "MPS IIIA-related symptom(s)" or "symptom(s)" refers to symptom(s) found in MPS IIIA patients as well as in MPS IIIA animal models. Such symptoms include but not limited to delayed speech; difficulty with social interactions and communication; sleep disturbances; progressive intellectual disability and the loss of previously acquired skills (developmental regression); seizures and movement disorders; a large head; a slightly enlarged liver (mild hepatomegaly); a soft out-pouching around the belly-button (umbilical hernia) or lower abdomen (inguinal hernia); short stature, joint stiffness, mild dysostosis multiplex, multiple skeletal abnormalities; chronic diarrhea; recurrent upper respiratory infections; recurrent ear infections; hearing impairment; vision problems; Asymmetric septal hypertrophy; Coarse facial features; Coarse hair; Dense calvaria; Dysostosis multiplex; Growth abnormality; Heparan sulfate excretion in urine; GAG accumulation in the cerebrospinal fluid (CSF), serum, urine and/or any other biological samples; abnormal expression and/or enzyme activity of N-acetyl-alpha-D-glucosaminidase (NAGLU) or N-sulfoglycosamine sulfohydrolase (IDUA); accumulation of GM2 and GM3; changed activity in lysosomal enzymes; accumulation of free unesterified cholesterol in the CNS; inflammatory response in the CNS and skeletal tissues; excess hair growth (Hirsutism); Hyperactivity; Ovoid thoracolumbar vertebrae; Splenomegaly; Synophrys; Thickened ribs; hernias; and a wobbly and erratic walk.

"Patient" or "subject" as used herein means a male or female human, dogs, and animal models used for clinical research. In one embodiment, the subject of these methods and compositions is a human diagnosed with MPS IIIA. In certain embodiments, the human subject of these methods and compositions is a prenatal, a newborn, an infant, a toddler, a preschool, a grade-schooler, a teen, a young adult or an adult. In a further embodiment, the subject of these methods and compositions is a pediatric MPS IIIA patient.

Clinical examination and urine tests (excess mucopolysaccharides are excreted in the urine) are the first steps in the diagnosis of an MPS disease. Enzyme assays measuring levels of enzyme activity in the blood, skin cells or a variety of cells are also used to provide definitive diagnosis of MPS IIIA. Various genetic testing detecting a mutation of SGSH associated with MPS IIIA is available. See, e.g., www.ncbi.nlm.nih.gov/gtr/conditions/-C0086647/; www.ncbi.nlm.nih.gov/gtr/all/tests/?term=C0086647[DISCUI]. Prenatal diagnosis using amniocentesis and chorionic villus sampling can verify if a fetus is affected with the disorder. Genetic counseling can help parents who have a family history of the mucopolysaccharidoses determine if they are carrying the mutated gene that causes the disorders. See, e.g., A Guide to Understanding MPS III, National MPS Society, 2008, mpssociety.org/learn/diseases/mps-iii/.

"Comprising" is a term meaning inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention. It should be understood that while various embodiments in the specification are presented using "comprising" language, under various circumstances, a related embodiment is also described using "consisting of" or "consisting essentially of" language.

It is to be noted that the term "a" or "an", refers to one or more, for example, "a vector", is understood to represent one or more vector(s). As such, the terms "a" (or "an"), "one or more," and "at least one" is used interchangeably herein.

As used herein, the term "about" means a variability of plus or minus 10% from the reference given, unless otherwise specified.

1. N-Sulfoglycosamine Sulfohydrolase (SGSH)

As used herein, the terms "N-sulfoglycosamine sulfohydrolase" and "SGSH" are used interchangeably with heparan-N-sulfatase, HNS. The invention includes any variant of SGSH protein expressed from the nucleic acid sequences provided herein, or a functional fragment thereof, which restores a desired function, ameliorates a symptom, improves symptoms associated with a MPS IIIA-related biomarker, or facilitate other treatment(s) for MPS IIIA when delivered in a composition or by a method as provided herein. Examples of a suitable biomarker for MPSIII includes that described in WO 2017/136533, which is incorporated herein by reference.

As used herein, the term "functional SGSH" means an enzyme having the amino acid sequence of the full-length wild-type (native) human SGSH (as shown in SEQ ID NO: 2 and UniProtKB accession number: P51688), a variant thereof, a mutant thereof with a conservative amino acid replacement, a fragment thereof, a full-length or a fragment of any combination of the variant and the mutant with a conservative amino acid replacement, which provides at least about 10%, at least about 20%, at least about 30%, at least about 40%, at least about 50%, at least about 60%, at least about 70%, at least about 75%, at least about 80%, at least about 90%, or about the same, or greater than 100% of the biological activity level of normal human SGSH. In some embodiment, a functional SGSH refers to a wild-type protein with sequence of SEQ ID NO: 2.

Examples of SGSH variants include but not limited to, V361I, which consists of the amino acid sequence of SEQ ID NO: 2 with an isoleucine (Ile, I) at the 361st amino acid instead of valine (Val, V) in the wild-type; M372I, which consists of the amino acid sequence of SEQ ID NO: 2 with an isoleucine (Ile, I) at the 372nd amino acid instead of methionine (Met, M) in the wild-type; V387M, which consists of the amino acid sequence of SEQ ID NO: 2 with a methionine (Met, M) at the 387th amino acid instead of valine (Val, V) in the wild-type; M394I, which consists of the amino acid sequence of SEQ ID NO: 2 with an isoleucine (Ile, I) at the 394th amino acid instead of methionine (Met, M) in the wild-type; and R456H, which consists of the amino acid sequence of SEQ ID NO: 2 with a histidine (His, H) at the 456th amino acid instead of arginine (Arg, R) in the wild-type. SGSH variants may also include any two, any three, any four or all five of the mutants of the amino acids at the positions identified above. Additional examples of SGSH variants may include those predicted by bioinformatic tools available to one of skill in the art. See, e.g., Ugrinov K G et al. A multiparametric computational algorithm for comprehensive assessment of genetic mutations in mucopolysaccharidosis type IIIA (Sanfilippo syndrome). PLoS One. 2015 Mar. 25; 10(3):e0121511. doi: 10.1371/journal.pone.0121511. eCollection 2015, which is incorporated herein by reference in its entirety.

As used herein, the "conservative amino acid replacement" or "conservative amino acid substitutions" refers to a change, replacement or substitution of an amino acid to a different amino acid with similar biochemical properties (e.g. charge, hydrophobicity and size), which is known by practitioners of the art. Also see, e.g. FRENCH et al. What is a conservative substitution? Journal of Molecular Evolution, March 1983, Volume 19, Issue 2, pp 171-175 and YAMPOLSKY et al. The Exchangeability of Amino Acids in Proteins, Genetics. 2005 August; 170(4): 1459-1472, each of which is incorporated herein by reference in its entirety.

A variety of assays exist for measuring SGSH expression and activity levels by conventional methods. See, e.g., Example 1 as described herein; www.ncbi.nlm.nih.gov/gtr/all/tests/?term=C0086647[DISCUI]&filter=method:1_2; testtype: clinical; Karpova E A et al, A fluorimetric enzyme assay for the diagnosis of Sanfilippo disease type A (MPS IIIA). J Inherit Metab Dis. 1996; 19(3):278-85; Tardieu M et al, Intracerebral administration of adeno-associated viral vector serotype rh.10 carrying human SGSH and SUMF1 cDNAs in children with mucopolysaccharidosis type IIIA disease: results of a phase I/II trial. Hum Gene Ther. 2014 June; 25(6):506-16. doi: 10.1089/hum.2013.238. Epub 2014 May 5; Whyte L S et al, Variables influencing fluorimetric N-sulfoglucosamine sulfohydrolase (SGSH) activity measurement in brain homogenates. Mol Genet Metab Rep. 2015 Oct. 22; 5:60-62. doi: 10.1016/j.ymgmr.2015.10.005. eCollection 2015 December; Hopwood J J et al. Diagnosis of Sanfilippo type A syndrome by estimation of sulfamidase activity using a radiolabelled tetrasaccharide substrate. Clin Chim Acta. 1982 Aug. 18; 123(3):241-50; each of which is incorporated by reference herein in its entirety.

In one aspect, a nucleic acid sequence which encodes a functional SGSH protein is provided. In one embodiment, the nucleic acid sequence is the wild-type coding sequence reproduced in SEQ ID NO: 3. In one embodiment, the nucleic acid sequence is at least about 60%, at least about 65%, at least about 70%, at least about 75%, at least about 80% identical thereto the wild-type hSGSH sequence of SEQ ID NO: 3. In one embodiment, the nucleic acid sequence is less than 83.3% identical to the wild-type hSGSH sequence of SEQ ID NO: 3.

A nucleic acid refers to a polymeric form of nucleotides and includes RNA, mRNA, cDNA, genomic DNA, peptide nucleic acid (PNA) and synthetic forms and mixed polymers of the above. A nucleotide refers to a ribonucleotide, deoxynucleotide or a modified form of either type of nucleotide (e.g., a peptide nucleic acid oligomer). The term also includes single- and double-stranded forms of DNA. The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

In certain embodiments, the nucleic acid molecules encoding a functional human SGSH (hSGSH), and other constructs encompassed by the present invention and useful in generating expression cassettes and vector genomes may be engineered for expression in yeast cells, insect cells or mammalian cells, such as human cells. Methods are known and have been described previously (e.g. WO 96/09378). A sequence is considered engineered if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in www. kazusa.jp/codon. Preferably more than one non-preferred codon, preferably most or all non-preferred codons, are replaced by codons that are more preferred. Preferably the most frequently used codons in an organism are used in an engineered sequence. Replacement by preferred codons generally leads to higher expression. It will also be understood by a skilled person that numerous different nucleic acid molecules can encode the same polypeptide as a result of the degeneracy of the genetic code. It is also understood that skilled persons may, using routine techniques, make nucleotide substitutions that do not affect the amino acid sequence encoded by the nucleic acid molecules to reflect the codon usage of any particular host organism in which the polypeptides are to be expressed. Therefore, unless otherwise specified, a "nucleic acid sequence encoding an amino acid sequence" includes all nucleotide sequences that are degenerate versions of each other and that encode the same amino acid sequence. Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScript, Life Technologies, Eurofins).

In one aspect, the SGSH coding sequence is an engineered sequence. In one embodiment, the engineered sequence is useful to improve production, transcription, expression or safety in a subject. In another embodiment, the engineered sequence is useful to increase efficacy of the resulting therapeutic compositions or treatment. In a further embodiment, the engineered sequence is useful to increase the efficacy of the functional SGSH protein being expressed, but may also permit a lower dose of a therapeutic reagent that delivers the functional protein to increase safety.

In one embodiment, the engineered SGSH coding sequence is characterized by improved translation rate as compared to wild-type SGSH coding sequences. In one embodiment, the SGSH coding sequence has less than 83.3% identical to the wild-type hSGSH sequence of SEQ ID NO: 3. In one embodiment, the SGSH coding sequence shares less than about 99%, less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 79%, less than about 78%, less than about 77%, less than about 76%, less than about 75%, less than about 74%, less than about 73%, less than about 72%, less than about 71%, less than about 70%, less than about 69%, less than about 68%, less than about 67%, less than about 66%, less than about 65%, less than about 64%, less than about 63%, less than about 62%, less than about 61% or less identity to the wild type SGSH coding sequence. In another embodiment, the SGSH coding sequence shares about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61% or less identity to the wild type SGSH coding sequence. In one embodiment, provided is an engineered nucleic acid sequence comprising a sequence of SEQ ID NO: 1, wherein the sequence encodes a functional hSGSH. In one embodiment, provided herein is an engineered nucleic acid sequence of SEQ ID NO: 1, or a nucleic acid sequence at least about 95% identical thereto, encoding a functional hSGSH. In another embodiment, the SGSH coding sequence is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity to SEQ ID NO: 1, wherein the sequence encodes a functional hSGSH.

By "engineered" is meant that the nucleic acid sequences encoding a functional SGSH protein described herein are assembled and placed into any suitable genetic element, e.g., naked DNA, phage, transposon, cosmid, episome, etc., which transfers the SGSH sequences carried thereon to a host cell, e.g., for generating non-viral delivery systems (e.g., RNA-based systems, naked DNA, or the like), or for generating viral vectors in a packaging host cell, and/or for delivery to a host cells in a subject. In one embodiment, the genetic element is a vector. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Multiple sequence alignment programs are also available for nucleic acid sequences. Examples of such programs include, "Clustal Omega", "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Identity may be determined by preparing an alignment of the sequences and through the use of a variety of algorithms and/or computer programs known in the art or commercially available (e.g., BLAST, ExPASy; Clustal Omega; FASTA; using, e.g., Needleman-Wunsch algorithm, Smith-Waterman algorithm). Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, "a desired function" refers to an SGSH enzyme activity at least about 20%, about 25%, about 30%, about 35%, about 40%, about 45%, about 50%, about 55%, about 60%, about 65%, about 70%, about 75%, about 80%, about 85%, about 90%, about 95%, or about 100% of a healthy control.

As used herein, the phrases "ameliorate a symptom", "improve a symptom" or any grammatical variants thereof, refer to reversal of an MPS IIIA-related symptoms, showdown or prevention of progression of an MPS IIIA-related symptoms. In one embodiment, the amelioration or improvement refers to the total number of symptoms in a patient after administration of the described composition(s) or use of the described method, which is reduced by about 5%, about 10%, about 20%, about 30%, about 40%, about 50%, about 60%, about 70%, about 80%, about 90%, about 95% compared to that before the administration or use. In another embodiment, the amelioration or improvement refers to the severity or progression of a symptom after administration of the described composition(s) or use of the described method, which is reduced by about 5%, about 10%, about 20%, about 30%, about 40%, about 50%, about 60%, about 70%, about 80%, about 90%, about 95% compared to that before the administration or use.

It should be understood that the compositions in the SGSH functional protein and SGSH coding sequence described herein are intended to be applied to other compositions, regiments, aspects, embodiments and methods described across the Specification.

2. Expression Cassette

In one aspect, provided is an expression cassette comprising an engineered nucleic acid sequence encoding a functional hSGSH, and a regulatory sequence which direct expression thereof. In one embodiment, an expression cassette comprising an engineered nucleic acid sequence as described herein which encodes a functional hSGSH, and a regulatory sequence which direct expression thereof.

As used herein, the term "expression" or "gene expression" refers to the process by which information from a gene is used in the synthesis of a functional gene product. The gene product may be a protein, a peptide, or a nucleic acid polymer (such as a RNA, a DNA or a PNA).

As used herein, an "expression cassette" refers to a nucleic acid polymer which comprises the coding sequences for a functional SGSH, promoter, and may include other regulatory sequences therefor, which cassette may be packaged into a vector.

As used herein, the term "regulatory sequence", or "expression control sequence" refers to nucleic acid sequences, such as initiator sequences, enhancer sequences, and promoter sequences, which induce, repress, or otherwise control the transcription of protein encoding nucleic acid sequences to which they are operably linked.

As used herein, the term "operably linked" refers to both expression control sequences that are contiguous with the nucleic acid sequence encoding the functional hSGSH and/or expression control sequences that act in trans or at a distance to control the transcription and expression thereof.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

In one embodiment, the regulatory sequence comprises a promoter. In one embodiment, the promoter is a chicken β-actin promoter. In a further embodiment, the promoter is a hybrid of a cytomegalovirus immediate-early enhancer and the chicken β-actin promoter (a CB7 promoter). In another embodiment, a suitable promoter may include without limitation, an elongation factor 1 alpha (EF1 alpha) promoter (see, e.g., Kim D W et al, Use of the human elongation factor 1 alpha promoter as a versatile and efficient expression system. Gene. 1990 Jul. 16; 91(2):217-23), a Synapsin 1 promoter (see, e.g., Kugler S et al, Human synapsin 1 gene promoter confers highly neuron-specific long-term transgene expression from an adenoviral vector in the adult rat brain depending on the transduced area. Gene Ther. 2003 February; 10(4):337-47), a neuron-specific enolase (NSE) promoter (see, e.g., Kim J et al, Involvement of cholesterol-rich lipid rafts in interleukin-6-induced neuroendocrine differentiation of LNCaP prostate cancer cells. Endocrinology. 2004 February; 145(2):613-9. Epub 2003 Oct. 16), or a CB6 promoter (see, e.g., Large-Scale Production of Adeno-Associated Viral Vector Serotype-9 Carrying the Human Survival Motor Neuron Gene, Mol Biotechnol. 2016 January; 58(1):30-6. doi: 10.1007/s12033-015-9899-5).

In one embodiment, the expression cassette is designed for expression and secretion in a human subject. In one embodiment, the expression cassette is designed for expression in the central nervous system (CNS), including the cerebral spinal fluid and brain. In a further embodiment, the expression cassette is useful for expression in both the CNS and in the liver. Suitable promoters may be selected, including but not limited to a constitutive promoter, a tissue-specific promoter or an inducible/regulatory promoter. Example of a constitutive promoter is chicken beta-actin promoter. A variety of chicken beta-actin promoters have been described alone, or in combination with various enhancer elements (e.g., CB7 is a chicken beta-actin promoter with cytomegalovirus enhancer elements; a CAG promoter, which includes the promoter, the first exon and first intron of chicken beta actin, and the splice acceptor of the rabbit beta-globin gene; a CBh promoter, S J Gray et al, Hu Gene Ther, 2011 September; 22(9): 1143-1153). Examples of promoters that are tissue-specific are well known for liver (albumin, Miyatake et al., (1997) *J. Virol.*, 71:5124-32; hepatitis B virus core promoter, Sandig et al., (1996) *Gene Ther.*, 3:1002-9; alpha-fetoprotein (AFP), Arbuthnot et al., (1996) *Hum. Gene Ther.*, 7:1503-14), neuron (such as neuron-specific enolase (NSE) promoter, Andersen et al., (1993) *Cell. Mol. Neurobiol.*, 13:503-15; neurofilament light-chain gene, Piccioli et al., (1991) *Proc. Natl. Acad. Sci. USA*, 88:5611-5; and the neuron-specific vgf gene, Piccioli et al., (1995) *Neuron,* 15:373-84), and other tissues. Alternatively, a regulatable promoter may be selected. See, e.g., WO 2011/126808B2, incorporated by reference herein.

In one embodiment, the regulatory sequence further comprises an enhancer. In one embodiment, the regulatory sequence comprises one enhancer. In another embodiment, the regulatory sequence contains two or more expression enhancers. These enhancers may be the same or may be different. For example, an enhancer may include an Alpha mic/bik enhancer or a CMV enhancer. This enhancer may be present in two copies which are located adjacent to one another. Alternatively, the dual copies of the enhancer may be separated by one or more sequences.

In one embodiment, the regulatory sequence further comprises an intron. In a further embodiment, the intron is a chicken beta-actin intron. Other suitable introns include those known in the art may by a human β-globulin intron, and/or a commercially available Promega® intron, and those described in WO 2011/126808.

In one embodiment, the regulatory sequence further comprises a Polyadenylation signal (polyA). In a further embodiment, the polyA is a rabbit globin poly A. See, e.g., WO 2014/151341. Alternatively, another polyA, e.g., a human growth hormone (hGH) polyadenylation sequence, an SV40 polyA, or a synthetic polyA may be included in an expression cassette.

It should be understood that the compositions in the expression cassette described herein are intended to be applied to other compositions, regiments, aspects, embodiments and methods described across the Specification.

3. Vector

In one aspect, provided herein is a vector comprising an engineered nucleic acid sequence encoding a functional human N-sulfoglycosamine sulfohydrolase (hSGSH) and a regulatory sequence which direct expression thereof in a target cell. In one embodiment, the hSGSH coding sequence is at least 96% identical to SEQ ID NO: 1. In a further embodiment, the hSGSH coding sequence is SEQ ID NO: 1.

A "vector" as used herein is a biological or chemical moiety comprising a nucleic acid sequence which can be introduced into an appropriate target cell for replication or expression of said nucleic acid sequence. Examples of a vector includes but not limited to a recombinant virus, a plasmid, Lipoplexes, a Polymersome, Polyplexes, a dendrimer, a cell penetrating peptide (CPP) conjugate, a magnetic particle, or a nanoparticle. In one embodiment, a vector is a nucleic acid molecule into which an exogenous or heterologous or engineered nucleic acid encoding a functional SGSH may be inserted, which can then be introduced into an appropriate target cell. Such vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and "artificial chromosomes". Conventional methods of generation, production, characterization or quantification of the vectors are available to one of skill in the art.

In one embodiment, the vector is a non-viral plasmid that comprises an expression cassette described thereof, e.g., "naked DNA", "naked plasmid DNA", RNA, and mRNA;

coupled with various compositions and nano particles, including, e.g., micelles, liposomes, cationic lipid—nucleic acid compositions, poly-glycan compositions and other polymers, lipid and/or cholesterol-based—nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, all of which are incorporated herein by reference.

In certain embodiments, the vector described herein is a "replication-defective virus" or a "viral vector" which refers to a synthetic or artificial viral particle in which an expression cassette containing a nucleic acid sequence encoding SGSH is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the nucleic acid sequence encoding SGSH flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

As used herein, a recombinant virus vector is an adeno-associated virus (AAV), an adenovirus, a bocavirus, a hybrid AAV/bocavirus, a herpes simplex virus or a lentivirus.

As used herein, the term "host cell" may refer to the packaging cell line in which a vector (e.g., a recombinant AAV) is produced. A host cell may be a prokaryotic or eukaryotic cell (e.g., human, insect, or yeast) that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. Examples of host cells may include, but are not limited to an isolated cell, a cell culture, an *Escherichia coli* cell, a yeast cell, a human cell, a non-human cell, a mammalian cell, a non-mammalian cell, an insect cell, an HEK-293 cell, a liver cell, a kidney cell, a cell of the central nervous system, a neuron, a glial cell, or a stem cell.

As used herein, the term "target cell" refers to any target cell in which expression of the functional SGSH is desired. In certain embodiments, the term "target cell" is intended to reference the cells of the subject being treated for MPS IIIA. Examples of target cells may include, but are not limited to, a liver cell, a kidney cell, a cell of the central nervous system, a neuron, a glial cell, and a stem cell. In certain embodiments, the vector is delivered to a target cell ex vivo. In certain embodiments, the vector is delivered to the target cell in vivo.

It should be understood that the compositions in the vector described herein are intended to be applied to other compositions, regiments, aspects, embodiments and methods described across the Specification.

4. Adeno-Associated Virus (AAV)

In one aspect, provided herein is a recombinant AAV (rAAV) comprising an AAV capsid and a vector genome packaged therein. The rAAV is for use in the treatment of Mucopolysaccharidosis III A (MPS IIIA). The vector genome comprises an AAV 5' inverted terminal repeat (ITR), an engineered nucleic acid sequence encoding a functional hSGSH as described herein, a regulatory sequence which direct expression of hSGSH in a target cell, and an AAV 3' ITR. In one embodiment, the hSGSH coding sequence is at least 95% identical to SEQ ID NO: 1. In a further embodiment, the hSGSH coding sequence is SEQ ID NO: 1.

In one embodiment, the regulatory sequence is as described above. In one embodiment, the vector genome comprises an AAV 5' inverted terminal repeat (ITR), an expression cassette as described herein, and an AAV 3' ITR.

In one embodiment, provided is a rAAV comprising an AAV serotype 9 (AAV9) capsid and a vector genome comprising a CB7 promoter expressing an engineered version of human N-sulfoglucosamine sulfohydrolase (hSGSH) with a rabbit beta-globin (rBG) polyA sequence. In a further embodiment, the rAAV vector genome comprises the sequence of SEQ ID NO: 4 (AAV.CB7.CI.hSGSHco.RBG). In one embodiment, the rAAV comprises an AAV9 capsid and a vector genome comprising the sequence of SEQ ID NO: 4, wherein the rAAV is represented as AAV9.CB7.CI.hSGSHco.RBG. In one embodiment, the rAAV expresses an engineered version of hSGSH comprising the amino acid sequence of SEQ ID NO: 5.

As used herein, a "vector genome" refers to the nucleic acid sequence packaged inside a vector. In one embodiment, the vector genome refers to the nucleic acid sequence packaged inside a rAAV capsid forming an rAAV vector. Such a nucleic acid sequence contains AAV inverted terminal repeat sequences (ITRs). In one embodiment, the ITRs are from an AAV different than that supplying a capsid. In a preferred embodiment, the ITR sequences from AAV2, or the deleted version thereof (ΔITR), which may be used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, AAV vector genome comprises an AAV 5' ITR, the SGSH coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The term "AAV" as used herein refers to naturally occurring adeno-associated viruses, adeno-associated viruses available to one of skill in the art and/or in light of the composition(s) and method(s) described herein, as well as artificial AAVs. An adeno-associated virus (AAV) viral vector is an AAV DNase-resistant particle having an AAV protein capsid into which is packaged expression cassette flanked by AAV inverted terminal repeat sequences (ITRs) for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. Various AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). These documents also describe other AAV which may be selected for generating AAV and are incorporated by reference. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, the AAVs commonly identified as AAV1, AAV2, AAV3, AAV4, AAV5, AAV6, AAV7, AAV8, AAV9, AAV8bp, AAV7M8 and AAVAnc80, variants of any of the known or mentioned AAVs or AAVs yet to be discovered or variants or mixtures thereof. See, e.g., WO 2005/033321, which is incorporated herein by reference. In one embodiment, the AAV capsid is an AAV9 capsid or variant thereof. In certain embodiments, the capsid protein is designated by a number or a combination of numbers and letters following the term "AAV" in the name of the rAAV vector.

As used herein, relating to AAV, the term "variant" means any AAV sequence which is derived from a known AAV sequence, including those with a conservative amino acid replacement, and those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3).

The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, Va.). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

As used herein, the terms "rAAV" and "artificial AAV" used interchangeably, mean, without limitation, a AAV comprising a capsid protein and a vector genome packaged therein, wherein the vector genome comprising a nucleic acid heterologous to the AAV. In one embodiment, the capsid protein is a non-naturally occurring capsid. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same rAAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, "AAV9 capsid" refers to the AAV9 having the amino acid sequence of (a) GenBank accession: AAS99264, is incorporated by reference herein and the AAV vp1 capsid protein is reproduced in SEQ ID NO: 6, and/or (b) the amino acid sequence encoded by the nucleotide sequence of GenBank Accession: AY530579.1: (nt 1..2211) (reproduced in SEQ ID NO: 7). Some variation from this encoded sequence is encompassed by the present invention, which may include sequences having about 99% identity to the referenced amino acid sequence in GenBank accession: AAS99264 and U.S. Pat. No. 7,906,111 (also WO 2005/033321) (i.e., less than about 1% variation from the referenced sequence). Such AAV may include, e.g., natural isolates (e.g., hu68 (described in U.S. Patent Applications No. 62/464,748, filed Feb. 28, 2017 and U.S. Patent Application No. 62/591,002, filed Nov. 27, 2019, both entitled "Novel Adeno-associated virus (AAV) Clade F Vector and Uses Therefore", and WO 2018/160582), hu31 or hu32), or variants of AAV9 having amino acid substitutions, deletions or additions, e.g., including but not limited to amino acid substitutions selected from alternate residues "recruited" from the corresponding position in any other AAV capsid aligned with the AAV9 capsid; e.g., such as described in U.S. Pat. Nos. 9,102,949, 8,927,514, US2015/349911; WO 2016/049230A11; U.S. Pat. Nos. 9,623,120; 9,585,971. However, in other embodiments, other variants of AAV9, or AAV9 capsids having at least about 95% identity to the above-referenced sequences may be selected. See, e.g., US Published Patent Application No. 2015/0079038. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, the rAAV as described herein is a self-complementary AAV. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

In certain embodiments, the rAAV described herein is nuclease-resistant. Such nuclease may be a single nuclease, or mixtures of nucleases, and may be endonucleases or exonucleases. A nuclease-resistant rAAV indicates that the AAV capsid has fully assembled and protects these packaged genomic sequences from degradation (digestion) during nuclease incubation steps designed to remove contaminating nucleic acids which may be present from the production process. In many instances, the rAAV described herein is DNase resistant.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid; a functional rep gene; an expression cassette as described herein flanked by AAV inverted terminal repeats (ITRs); and sufficient helper functions to permit packaging of the expression cassette into the AAV capsid protein. Also provided herein is the host cell which contains a nucleic acid sequence encoding an AAV capsid; a functional rep gene; a vector genome as described; and sufficient helper functions to permit packaging of the vector genome into the AAV capsid protein. In one embodiment, the host cell is a HEK 293 cell. These methods are described in more detail in WO2017160360 A2, which is incorporated by reference herein.

Other methods of producing rAAV available to one of skill in the art may be utilized. Suitable methods may include without limitation, baculovirus expression system or production via yeast. See, e.g., Robert M. Kotin, Large-scale recombinant adeno-associated virus production. Hum Mol Genet. 2011 Apr. 15; 20(R1): R2-R6. Published online 2011 Apr. 29. doi: 10.1093/hmg/ddr141; Aucoin M G et al., Production of adeno-associated viral vectors in insect cells using triple infection: optimization of baculovirus concentration ratios. Biotechnol Bioeng. 2006 Dec. 20; 95(6):1081-92; SAMI S. THAKUR, Production of Recombinant Adeno-associated viral vectors in yeast. Thesis presented to the Graduate School of the University of Florida, 2012; Kondratov O et al. Direct Head-to-Head Evaluation of Recombinant Adeno-associated Viral Vectors Manufactured in Human versus Insect Cells, Mol Ther. 2017 Aug. 10. pii: S1525-0016(17)30362-3. doi: 10.1016/j.ymthe.2017.08.003. [Epub ahead of print]; Mietzsch M et al, OneBac 2.0: Sf9 Cell Lines for Production of AAV1, AAV2, and AAV8 Vectors with Minimal Encapsidation of Foreign DNA. Hum Gene Ther Methods. 2017 February; 28(1):15-22. doi: 10.1089/hgtb.2016.164.; Li L et al. Production and characterization of novel recombinant adeno-associated virus replicative-form genomes: a eukaryotic source of DNA for gene transfer. PLoS One. 2013 Aug. 1; 8(8):e69879. doi: 10.1371/journal.pone.0069879. Print 2013; Galibert L et al, Latest developments in the large-scale production of adeno-associated virus vectors in insect cells toward the treatment of neuromuscular diseases. J Invertebr Pathol. 2011 July; 107 Suppl:S80-93. doi: 10.1016/j.jip.2011.05.008; and Kotin R M, Large-scale recombinant adeno-associated virus production. Hum Mol Genet. 2011 Apr. 15; 20(R1):R2-6. doi: 10.1093/hmg/ddr141. Epub 2011 Apr. 29.

A two-step affinity chromatography purification at high salt concentration followed by anion exchange resin chromatography are used to purify the vector drug product and to remove empty capsids. These methods are described in more detail in WO 2017/160360 entitled "Scalable Purification Method for AAV9", which is incorporated by reference herein. In brief, the method for separating rAAV9 particles having packaged genomic sequences from genome-deficient AAV9 intermediates involves subjecting a suspension comprising recombinant AAV9 viral particles and AAV 9 capsid intermediates to fast performance liquid chromatography, wherein the AAV9 viral particles and AAV9 intermediates are bound to a strong anion exchange resin equilibrated at a pH of 10.2, and subjected to a salt gradient while monitoring eluate for ultraviolet absorbance at about 260 and about 280. Although less optimal for rAAV9, the pH may be in the range of about 10.0 to 10.4. In this method, the AAV9 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured.

Conventional methods for characterization or quantification of rAAV are available to one of skill in the art. To calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles. Generally, methods for assaying for empty capsids and AAV vector particles with packaged genomes have been known in the art. See, e.g., Grimm et al., *Gene Therapy* (1999) 6:1322-1330; Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers.

The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

Methods for determining the ratio among vp 1, vp2 and vp3 of capsid protein are also available. See, e.g., Vamseedhar Rayaprolu et al, Comparative Analysis of Adeno-Associated Virus Capsid Stability and Dynamics, J Virol. 2013 December; 87(24): 13150-13160; Buller R M, Rose J A. 1978. Characterization of adenovirus-associated virus-induced polypeptides in KB cells. J. Virol. 25:331-338; and Rose J A, Maizel J V, Inman J K, Shatkin A J. 1971. Structural proteins of adenovirus-associated viruses. J. Virol. 8:766-770.

As used herein, the term "treatment" or "treating" refers to composition(s) and/or method(s) for the purposes of amelioration of one or more symptoms of MPS IIIA, restore of a desired function of SGSH, or improvement of biomarker of disease. In some embodiments, the term "treatment" or "treating" is defined encompassing administering to a subject one or more compositions described herein for the purposes indicated herein. "Treatment" can thus include one or more of reducing onset or progression of MPS IIIA, preventing disease, reducing the severity of the disease symptoms, retarding their progression, removing the disease symptoms, delaying progression of disease, or increasing efficacy of therapy in a given subject.

It should be understood that the compositions in the rAAV described herein are intended to be applied to other compositions, regiments, aspects, embodiments and methods described across the Specification.

5. Pharmaceutical Composition

In one aspect, provided herein is a pharmaceutical composition comprising a vector as described herein in a formulation buffer. In one embodiment, the pharmaceutical composition is suitable for co-administering with a functional hSGSH protein or a functional Sulfatase-modifying factor 1 (SUMF1). In one embodiment, provided is a pharmaceutical composition comprising a rAAV as described herein in a formulation buffer. In one embodiments, the rAAV is formulated at about $1\times10^9$ genome copies (GC)/mL to about $1\times10^{14}$ GC/mL. In a further embodiment, the rAAV is formulated at about $3\times10^9$ GC/mL to about $3\times10^{13}$ GC/mL. In yet a further embodiment, the rAAV is formulated at about $1\times10^9$ GC/mL to about $1\times10^{13}$ GC/mL. In one embodiment, the rAAV is formulated at least about $1\times10^{11}$ GC/mL.

In one embodiment, the formulation further comprises a surfactant, preservative, excipients, and/or buffer dissolved in the aqueous suspending liquid. In one embodiment, the buffer is PBS. In another embodiment, the buffer is an artificial cerebrospinal fluid (aCSF), e.g., Eliott's formulation buffer; or Harvard apparatus perfusion fluid (an artificial CSF with final Ion Concentrations (in mM): Na 150; K 3.0; Ca 1.4; Mg 0.8; P 1.0; Cl 155). Various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

Suitably, the formulation is adjusted to a physiologically acceptable pH, e.g., in the range of pH 6 to 8, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of 6.8 to about 7.2 may be desired. However, other pHs within the broadest ranges and these subranges may be selected for other route of delivery.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly (propylene oxide)) flanked by two hydrophilic chains of polyoxyethylene (poly (ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate.7H2O), potassium chloride, calcium chloride (e.g., calcium chloride.2H2O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical].

In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA Additionally provided is a pharmaceutical composition comprising a pharmaceutically acceptable carrier and a vector comprising a nucleic acid sequence encoding a functional SGSH as described herein. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. Delivery vehicles such as liposomes, nanocapsules, microparticles, microspheres, lipid particles, vesicles, and the like, may be used for the introduction of the compositions of the present invention into suitable host cells. In particular, the rAAV vector may be formulated for delivery either encapsulated in a lipid particle, a liposome, a vesicle, a nanosphere, or a nanoparticle or the like. In one embodiment, a therapeutically effective amount of said vector is included in the pharmaceutical composition. The selection of the carrier is not a limitation of the present invention. Other conventional pharmaceutically acceptable carrier, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The phrase "pharmaceutically-acceptable" refers to molecular entities and compositions that do not produce an allergic or similar untoward reaction when administered to a host.

As used herein, the term "dosage" or "amount" can refer to the total dosage or amount delivered to the subject in the course of treatment, or the dosage or amount delivered in a single unit (or multiple unit or split dosage) administration.

Also, the replication-defective virus compositions can be formulated in dosage units to contain an amount of replication-defective virus that is in the range of about $1.0 \times 10^9$ GC to about $1.0 \times 10^{16}$ GC (to treat an average subject of 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

In one embodiment, the pharmaceutical composition comprising a rAAV as described herein is administrable at a dose of about $1 \times 10^9$ GC per gram of brain mass to about $1 \times 10^{14}$ GC per gram of brain mass.

The aqueous suspension or pharmaceutical compositions described herein are designed for delivery to subjects in need thereof by any suitable route or a combination of different routes. In one embodiment, the pharmaceutical composition is formulated for delivery via intracerebroventricular (ICV), intrathecal (IT), or intracisternal injection. In one embodiment, the compositions described herein are designed for delivery to subjects in need thereof by intravenous injection. Alternatively, other routes of administration may be selected (e.g., oral, inhalation, intranasal, intratracheal, intraarterial, intraocular, intramuscular, and other parenteral routes).

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular, suboccipital/intracisternal, and/or C1-2 puncture. For example, material may be introduced for diffusion throughout the subarachnoid space by means of lumbar puncture. In another example, injection may be into the cisterna magna. Intracisternal delivery may increase vector diffusion and/or reduce toxicity and inflammation caused by the administration. See, e.g., Christian Hinderer et al, Widespread gene transfer in the central nervous system of cynomolgus macaques following delivery of AAV9 into the cisterna magna, Mol Ther Methods Clin Dev. 2014; 1: 14051. Published online 2014 Dec. 10. doi: 10.1038/mtm.2014.51.

Figure 6A:
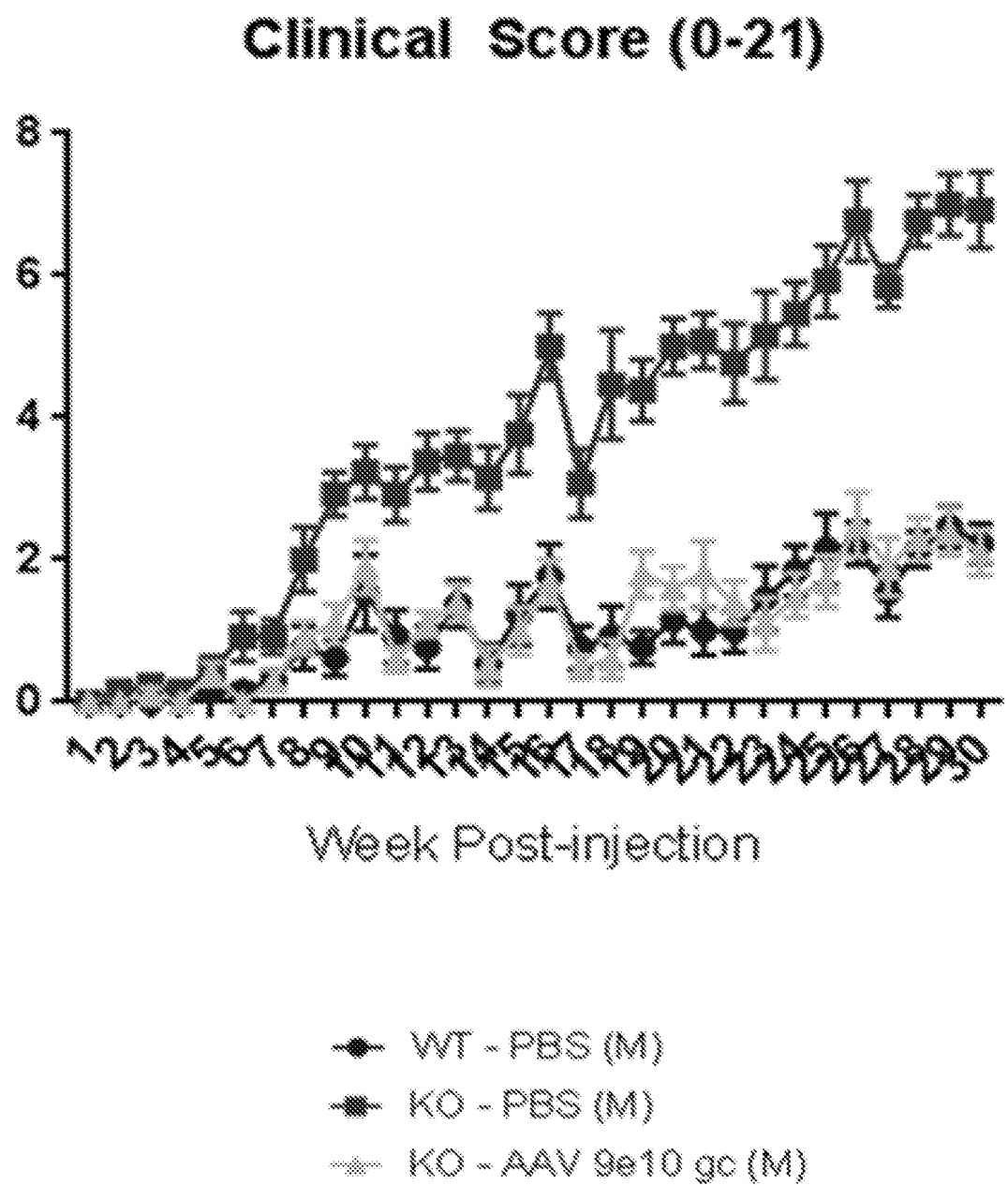
FIGS. 6A and 6B provides clinical scores for mice in a long-term study following AAV9.CB7.CI.hSGSH.rBG administration. Mice were injected at with high dose of AAV9.CB7.CI.hSGSH.rBG (9×1010 GC, ICV) at 2 months of age and evaluated weekly. Scores are shown for male (FIG. 6A) and female (FIG. 6B) mice. Control groups of wildtype (WT) and MPS IIIa (KO) mice received PBS injections.
Figure 6B:
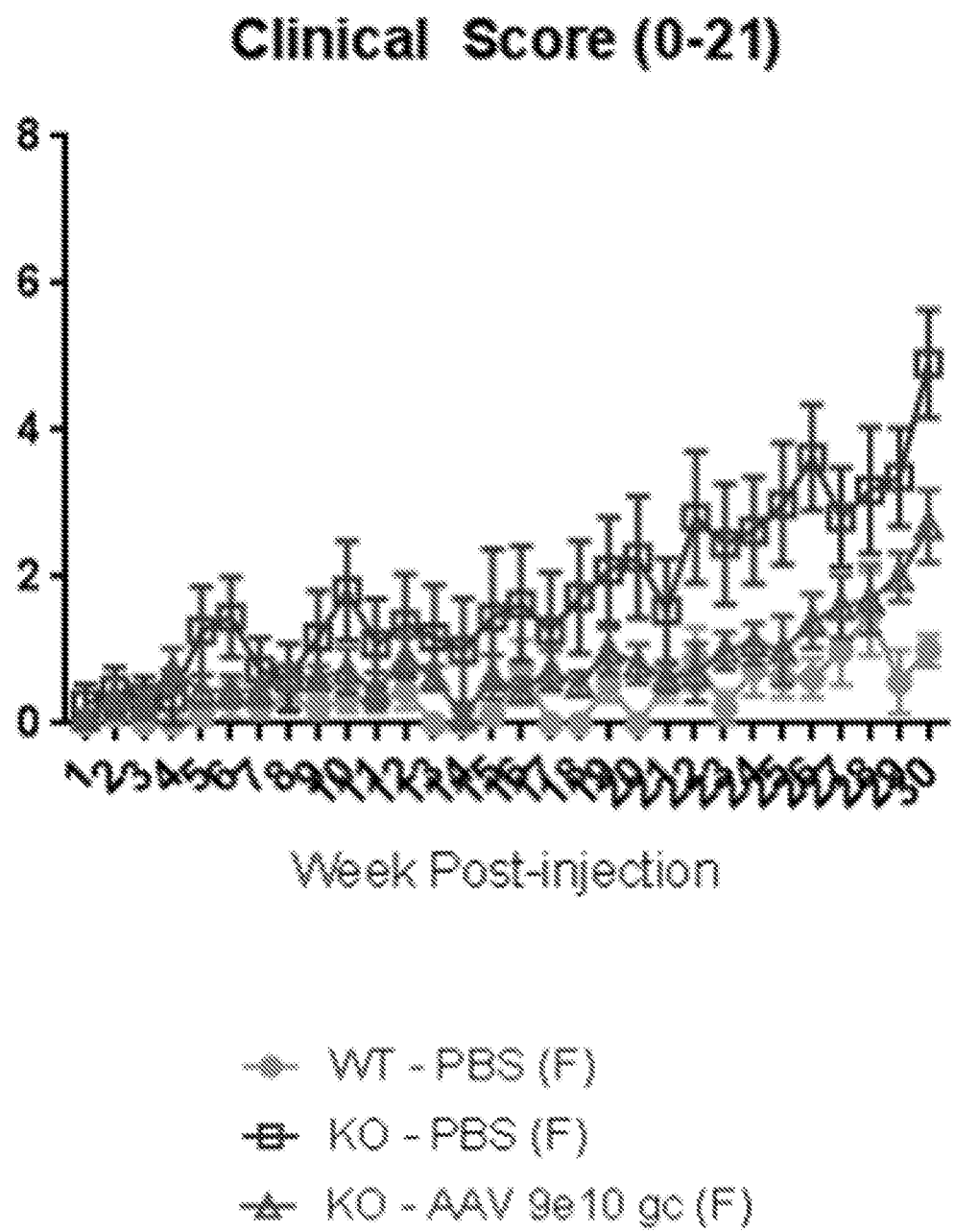

As used herein, the terms "intracisternal delivery" or "intracisternal administration" refer to a route of administration for drugs directly into the cerebrospinal fluid of the brain ventricles or within the cisterna magna cerebellomedularis, more specifically via a suboccipital puncture or by direct injection into the cisterna magna or via permanently positioned tube. FIG. 6 provides an illustration as to how an intracisternal injection would be made.

It should be understood that the compositions in the pharmaceutical composition described herein are intended to be applied to other compositions, regiments, aspects, embodiments and methods described across the Specification.

6. Method of Treatment

In one aspect, provided herein is a method of treating a human subject diagnosed with MPS IIIA. Currently, when there is a clinical suspicion of MPS III, the first step is the request of a quantitative test to detect the presence of GAGs in urine through spectrophotometric methods using dimethylmethylene blue (DMB). The DMB test is based on the union of GAGs to the dimethylmethylene blue and the quantification of the GAG-DMB complex with a spectrophotometer. The sensitivity of this test is 100%, with a specificity of 75-100%. A negative result when detecting GAGs in urine does not rule out the existence of MPS III due to the fact that in some patients with attenuated forms of the disease, the levels of GAGs excretion with healthy controls can overlap and the increased excretion of heparan sulfate in the MPS III can be ignored. The current gold standard technique for diagnosis is the determination of enzyme activity in cultured skin fibroblasts, leukocytes, plasma or serum. The specific diagnosis of MPS IIIA is confirmed by showing a decrease or absence of one of the SGSH enzymatic activities involved in the degradation of heparan sulfate in the patient's leukocytes or fibroblasts; the reduction should be less than 10% when compared to the activity in healthy individuals, with normalcy in other sulfatases. Because the disease due to deficiency in multiple sulfatases also shows a reduction in the activity of the heparan N-sulfatase, N-acetylglucosamine 6-sulfatase and other sulfatases, biochemical analysis of at least other sulfatase is required to confirm the diagnosis of MPS III and thus rule out multiple sulfatases deficiency. However, the method of diagnosis is not a limitation of the present invention and other suitable methods may be selected.

The method comprises administering to a subject a suspension of a vector as described herein. In one embodiment, the method comprises administering to a subject a suspension of a rAAV as described herein in a formulation buffer at a dose of about $1 \times 10^9$ GC per gram of brain mass to about $1 \times 10^{14}$ GC per gram of brain mass.

The composition(s) and method(s) provided herein achieve efficacy in treating a subject in need with MPS IIIA. Efficacy of the method in a subject can be shown by assessing (a) an increase in SGSH enzymatic activity; (b) amelioration of a MPS IIIA symptom; (c) improvement of MPS IIIA-related biomarkers, e.g., GAG levels polyamine (e.g., spermine) levels in the cerebrospinal fluid (CSF), serum, urine and/or other biological samples; or (e) facilitation of any treatment(s) for MPS IIIA. In certain embodiments, efficacy may be determined by monitoring cognitive improvement and/or anxiety correction, gait and/or mobility improvement, reduction in tremor frequency and/or severity, reduction in clasping/spasms, improvements in posture, improvements in corneal opacity. Additionally or alternatively, efficacy of the method may be predicted based on an animal model. One example of a suitable murine model is described in Example 1. In another embodiment, a multi-parameter grading scale was developed to evaluate disease correction and response to the MPSIIIA vector therapy described herein in an animal model. See, FIG. 5, incorporated herein by reference. Animals are assigned a score based on an assessment of a combination of tremor, posture, fur quality, clasping, corneal clouding, and gait/mobility. In certain embodiments, any combination of one or more of these factors may be used to demonstrate efficacy, alone, or in combination with other factors. See, e.g., Burkholder et al. Curr Protoc Mouse Biol. June 2012, 2:145-65; Tumpey et al. J Virol. May 1998, 3705-10; and Guyenet et al. J Vis Exp, May 2010, 39; 1787). Cognitive improvement and anxiety correction of treated animals is evaluated by assessing movement in an open field (i.e. beam break measurement as described, e.g., in Tatem et al. J Vis Exp, 2014, (91):51785) and the elevated plus maze assay (as described, e.g., in Walf and Frye, Nat Protoc, 2007, 2(2): 322-328.

As used herein, "facilitation of any treatment(s) for MPS IIIA" or any grammatical variant thereof, refers to a decreased dosage or a lower frequency of a treatment of MPS IIIA in a subject other than the composition(s) or method(s) which is/are firstly disclosed in the invention, compared to that of a standard treatment without administration of the described composition(s) and use of the described method(s). Examples of suitable treatment facilitated by the composition(s) or method(s) described herein might include, but not limited to, medications used to relieve symptoms (such as seizures and sleep disturbances) and improve quality of life; hematopoietic stem cell transplantation, such as bone marrow transplantation or umbilical cord blood transplantation; enzyme replacement therapies (ERT) via intravenous administration or intracerebroventricular infusion; and any combination thereof. In one embodiment, the described method results in the subject demonstrating an improvement of biomarkers related to MPS IIIA.

An "increase in SGSH enzymatic activity" is used interchangeably with the term "increase in desired SGSH function", and refers to a SGSH activity at least about 5%, 10%, 15%, 20%, about 25%, about 30%, about 35%, about 40%, about 45%, about 50%, about 55%, about 60%, about 65%, about 70%, about 75%, about 80%, about 85%, about 90%, about 95%, or about 100% of the SGSH enzyme range for a healthy patient. The SGSH enzymatic activity might be measured by an assay as described herein. In one embodiment, the SGSH enzymatic activity might be measured in the serum, plasma, blood, urine, CSF, or another biological sample. In one embodiment, administration of the composition as described herein, or use of the method as described herein, result in an increase in SGSH enzymatic activity in serum, plasma, saliva, urine or other biological samples. Alternatively, CSF GAG levels and other CSF biomarkers such as spermine levels may be measured to determine therapeutic effect. See. e.g., WO 2017/136533.

Neurocognition can be determined by conventional methods, See. e.g., WO 2017/136500 A1. Prevention of neurocognitive decline refers to a slowdown of a neurocognitive decline of the subject administered with the composition described herein or received the method described herein by at least about 5%, at least about 20%, at least about 20%, about 25%, about 30%, about 35%, about 40%, about 45%, about 50%, about 55%, about 60%, about 65%, about 70%, about 75%, about 80%, about 85%, about 90%, about 95%, or about 100% compared to that of a MPS IIIA patient.

As used herein, the terms "biomarker" or "MPS IIIA-related biomarker" refer to presence, concentration, expression level or activity of a biological or chemical molecular in a biological sample of a subject which correlates to progression or development of MPS IIIA in a positive or negative matter. In one embodiment, the biomarker is GAG levels in the cerebrospinal fluid (CSF), serum, urine, skin fibroblasts, leukocytes, plasma, or any other biological samples. In another embodiment, the biomarker is assessed using clinical chemistry. In yet another embodiment, the biomarker is liver or spleen volumes. In one embodiment, the biomarker is the activity of the heparan N-sulfatase, N-acetylglucosamine 6-sulfatase and other sulfatases. In another embodiment, the biomarker is spermine level in CSF, serum, or another biological sample. In yet another embodiment, the biomarker is lysosomal enzyme activity in serum, CSF, or another biological sample. In one embodiment, the biomarker is assessed via magnetic resonance imaging (MRI) of brain. In another embodiment, the biomarker is a neurocognitive score measured by a neurocognitive developmental test. The phrase "improvement of biomarker" as used herein means a reduction in a biomarker positively correlating to the progression of the disease, or an increase in a biomarker negatively correlating to the progression of the disease, wherein the reduction or increase is at least about 5%, at least about 20%, at least about 20%, about 25%, about 30%, about 35%, about 40%, about 45%, about 50%, about 55%, about 60%, about 65%, about 70%, about 75%, about 80%, about 85%, about 90%, about 95%, or about 100% compared to that before administration of the composition as described herein or use of the method as described herein.

In one embodiment, the method further comprises detecting or monitoring biomarkers related to MPS IIIA in the subject prior to initiation of therapy with therapy provided herein. In certain embodiments, the method comprises detection of biomarker which is a polyamine (such as spermine) in a sample from a subject (see WO/2017/136533, which is incorporated herein by reference). In certain embodiments, spermine concentration levels in a patient sample are detected to monitor the effectiveness of a treatment for MPSIII using the vector as described herein.

Currently, patients with MPSIIIA are not considered candidates for bone marrow transplantation (BMT), Substrate Reduction Therapy (SRT) or enzyme replacement therapy (ERT). However, in certain embodiments, a gene therapy patient treated with a vector expressing the SGSH described herein has, at a minimum, sufficient enzyme expression levels that any sub-normal range enzyme levels can be treated with ERT or SRT. Such ERT may be a co-therapy in which the dose of the ERT is monitored and modulated for months or years post-vector dosing. Additionally or alternatively, a SRT may be a co-therapy in which the dose of the SRT is monitored and modulated for months or years post-vector dosing.

Thus, in one embodiment, the suspension is suitable for co-administering with a functional hSGSH protein or a functional SUMF1 protein.

In one embodiment, the suspension is delivered into the subject in need intracerebroventricularly, intrathecally, intracisternally or intravenously.

In one embodiment, the suspension has a pH of about 7.28 to about 7.32.

As used herein, an enzyme replacement therapy (ERT) is a medical treatment that consists in replacing an enzyme in patients where a particular enzyme is deficient or absent. The enzyme is usually produced as a recombinant protein and administered to the patient. In one embodiment, the enzyme is a functional SGSH. In another embodiment, the enzyme is a recombinant protein comprising a functional SGSH. Systemic, intrathecal, intracerebroventricular or intracisternal delivery can be accomplished using ERT. As used herein, an Substrate Reduction Therapy (SRT) refers to a therapy using a small molecule drug to partially inhibit the biosynthesis of the compounds, which accumulate in the absence of SGSH. In one embodiment, the SRT is a therapy via genistein. See, e.g., Ritva Tikkanen et al, Less Is More: Substrate Reduction Therapy for Lysosomal Storage Disorders. Int J Mol Sci. 2016 July; 17(7): 1065. Published online 2016 Jul. 4. doi: 10.3390/ijms17071065; Delgadillo V et al, Genistein supplementation in patients affected by Sanfilippo disease. J Inherit Metab Dis. 2011 October; 34(5):1039-44. doi: 10.1007/s10545-011-9342-4. Epub 2011 May 10; and de Ruijter J et al, Genistein in Sanfilippo disease: a randomized controlled crossover trial. Ann Neurol. 2012 January; 71(1):110-20. doi: 10.1002/ana.22643.

Suitable volumes for delivery of these doses and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

In one embodiment, the rAAV as described herein is administrable at a dose of about $1 \times 10^9$ GC per gram of brain mass to about $1 \times 10^{14}$ GC per gram of brain mass. In certain embodiments, the rAAV is co-administered systemically at a dose of about $1 \times 10^9$ GC per kg body weight to about $1 \times 10^{13}$ GC per kg body weight In one embodiment, the subject is delivered a therapeutically effective amount of the vectors described herein. As used herein, a "therapeutically effective amount" refers to the amount of the composition comprising the nucleic acid sequence encoding hSGSH which delivers and expresses in the target cells an amount of enzyme sufficient to achieve efficacy. In one embodiment, the dosage of the vector is about $1 \times 10^9$ GC per gram of brain mass to about $1 \times 10^{13}$ genome copies (GC) per gram (g) of brain mass, including all integers or fractional amounts within the range and the endpoints. In another embodiment, the dosage is $1 \times 10^{10}$ GC per gram of brain mass to about $1 \times 10^{13}$ GC per gram of brain mass. In specific embodiments, the dose of the vector administered to a patient is at least about $1.0 \times 10^9$ GC/g, about $1.5 \times 10^9$ GC/g, about $2.0 \times 10^9$ GC/g, about $2.5 \times 10^9$ GC/g, about $3.0 \times 10^9$ GC/g, about $3.5 \times 10^9$ GC/g, about $4.0 \times 10^9$ GC/g, about $4.5 \times 10^9$ GC/g, about $5.0 \times 10^9$ GC/g, about $5.5 \times 10^9$ GC/g, about $6.0 \times 10^9$ GC/g, about $6.5 \times 10^9$ GC/g, about $7.0 \times 10^9$ GC/g, about $7.5 \times 10^9$ GC/g, about $8.0 \times 10^9$ GC/g, about $8.5 \times 10^9$ GC/g, about $9.0 \times 10^9$ GC/g, about $9.5 \times 10^9$ GC/g, about $1.0 \times 10^{10}$ GC/g, about $1.5 \times 10^{10}$ GC/g, about $2.0 \times 10^{10}$ GC/g, about $2.5 \times 10^{10}$ GC/g, about $3.0 \times 10^{10}$ GC/g, about $3.5 \times 10^{10}$ GC/g, about $4.0 \times 10^{10}$ GC/g, about $4.5 \times 10^{10}$ GC/g, about $5.0 \times 10^{10}$ GC/g, about $5.5 \times 10^{10}$ GC/g, about $6.0 \times 10^{10}$ GC/g, about $6.5 \times 10^{10}$ GC/g, about $7.0 \times 10^{10}$ GC/g, about $7.5 \times 10^{10}$ GC/g, about $8.0 \times 10^{10}$ GC/g, about $8.5 \times 10^{10}$ GC/g, about $9.0 \times 10^{10}$ GC/g, about $9.5 \times 10^{10}$ GC/g, about $1.0 \times 10^{11}$ GC/g, about $1.5 \times 10^{11}$ GC/g, about $2.0 \times 10^{11}$ GC/g, about $2.5 \times 10^{11}$ GC/g, about $3.0 \times 10^{11}$ GC/g, about $3.5 \times 10^{11}$ GC/g, about $4.0 \times 10^{11}$ GC/g, about $4.5 \times 10^{11}$ GC/g, about $5.0 \times 10^{11}$ GC/g, about $5.5 \times 10^{11}$ GC/g, about $6.0 \times 10^{11}$ GC/g, about $6.5 \times 10^{11}$ GC/g, about $7.0 \times 10^{11}$ GC/g, about $7.5 \times 10^{11}$ GC/g, about $8.0 \times 10^{11}$ GC/g, about $8.5 \times 10^{11}$ GC/g, about $9.0 \times 10^{11}$ GC/g, about $9.5 \times 10^{11}$ GC/g, about $1.0 \times 10^{12}$ GC/g, about $1.5 \times 10^{12}$ GC/g, about $2.0 \times 10^{12}$ GC/g, about $2.5 \times 10^{12}$ GC/g, about $3.0 \times 10^{12}$ GC/g, about $3.5 \times 10^{12}$ GC/g, about $4.0 \times 10^{12}$ GC/g, about $4.5 \times 10^{12}$ GC/g, about $5.0 \times 10^{12}$ GC/g, about $5.5 \times 10^{12}$ GC/g, about $6.0 \times 10^{12}$ GC/g, about $6.5 \times 10^{12}$ GC/g, about $7.0 \times 10^{12}$ GC/g, about $7.5 \times 10^{12}$ GC/g, about $8.0 \times 10^{12}$ GC/g, about $8.5 \times 10^{12}$ GC/g, about $9.0 \times 10^{12}$ GC/g, about $9.5 \times 10^{12}$ GC/g, about $1.0 \times 10^{13}$ GC/g, about $1.5 \times 10^{13}$ GC/g, about $2.0 \times 10^{13}$ GC/g, about $2.5 \times 10^{13}$ GC/g, about $3.0 \times 10^{13}$ GC/g, about $3.5 \times 10^{13}$ GC/g, about $4.0 \times 10^{13}$ GC/g, about $4.5 \times 10^{13}$ GC/g, about $5.0 \times 10^{13}$ GC/g, about $5.5 \times 10^{13}$ GC/g, about $6.0 \times 10^{13}$ GC/g, about $6.5 \times 10^{13}$ GC/g, about $7.0 \times 10^{13}$ GC/g, about $7.5 \times 10^{13}$ GC/g, about $8.0 \times 10^{13}$ GC/g, about $8.5 \times 10^{13}$ GC/g, about $9.0 \times 10^{13}$ GC/g, about $9.5 \times 10^{13}$ GC/g, or about $1.0 \times 10^{14}$ GC/g brain mass.

In one embodiment, the method further comprises the subject receives an immunosuppressive co-therapy Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an antimetabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor- (CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent.

In certain embodiments, the immunosuppressive therapy may be started 0, 1, 2, 7, or more days prior to the gene therapy administration. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week (7 days), about 60 days, or longer, as needed. In certain embodiments, a tacrolimus-free regimen is selected.

In certain embodiment, the method comprises measurement of serum anti-hSGSH antibodies. Suitable assays of measuring anti-hSGSH antibody are available, See, e.g., Example 1.

In one embodiment, the rAAV as described herein is administered once to the subject in need. In another embodiment, the rAAV is administered more than once to the subject in need.

It should be understood that the compositions in the method described herein are intended to be applied to other compositions, regiments, aspects, embodiments and methods described across the Specification.

7. Kit

In certain embodiments, a kit is provided which includes a concentrated vector suspended in a formulation (optionally frozen), optional dilution buffer, and devices and components required for intrathecal, intracerebroventricular or intracisternal administration. In another embodiment, the kit may additional or alternatively include components for intravenous delivery. In one embodiment, the kit provides sufficient buffer to allow for injection. Such buffer may allow for about a 1:1 to a 1:5 dilution of the concentrated vector, or more. In other embodiments, higher or lower amounts of buffer or sterile water are included to allow for dose titration and other adjustments by the treating clinician. In still other embodiments, one or more components of the device are included in the kit. Suitable dilution buffer is available, such as, a saline, a phosphate buffered saline (PBS) or a glycerol/PBS.

It should be understood that the compositions in kit described herein are intended to be applied to other compositions, regiments, aspects, embodiments and methods described across the Specification.

8. Device

In one aspect, the vectors provided herein may be administered intrathecally via the method and/or the device described, e.g., in WO 2017/136500, which is incorporated herein by reference in its entirety. Alternatively, other devices and methods may be selected. In summary, the method comprises the steps of advancing a spinal needle into the cisterna magna of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient. This method and this device may each optionally be used for intrathecal delivery of the compositions provided herein. Alternatively, other methods and devices may be used for such intrathecal delivery.

It should be understood that the compositions in the device described herein are intended to be applied to other compositions, regiments, aspects, embodiments and methods described across the Specification.

EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1: Methods

A. Vector—AAV9.CB7.CI.hSGSHco.rBG

A hSGSH (MPS IIIA) engineered sequence as shown in SEQ ID NO: 1 was cloned into an expression construct containing a CB7 promoter (a hybrid of a cytomegalovirus immediate-early enhancer and the chicken β-actin promoter), chicken β-actin intron (CI), and rabbit beta globin (rBG) polyadenylation sequence. The expression construct was flanked by AAV2 inverted terminal repeats and an AAV9 trans plasmid was used for encapsidation.

AAV vectors were manufactured by Penn Vector Core with iodixanol gradient method. See, Lock, M., et al., Rapid, Simple, and Versatile Manufacturing of Recombinant Adeno-Associated Viral Vectors at Scale. Human Gene Therapy, 2010. 21(10): p. 1259-1271. The purified vectors were titrated with Droplet Digital PCR (Lock, M., et al., Absolute Determination of Single-Stranded and Self-Complementary Adeno-Associated Viral Vector Genome Titers by Droplet Digital PCR. Human Gene Therapy Methods, 2014. 25(2): p. 115-125) for MPS IIIA.

Dubelco's phosphate buffer saline (dPBS) without calcium and magnesium was used as control article (vehicle control) and diluent for vector. The test article was diluted with sterile phosphate buffered saline (PBS) to the appropriate concentration for each dose group. Diluted vector was kept on wet ice and injected to the animals within 4 hours after dilution.

B. Animal Procedures

All animal protocols were approved by the Institutional Animal Care and Use Committee of the University of Pennsylvania. Mice colony with spontaneous murine SGSH mutant was maintained in the Gene Therapy Program vivarium at the University of Pennsylvania. All offspring were genotyped by PCR analysis of tail snip DNA using an automated system (Transnetyx Inc, 8110 Cordova Road Suite 119 Cordova, Tenn. 38016). Mice were grouped based on their genotype after weaning and were not mixed after that to prevent fighting; all animals in a given cage received the same treatment. Cages were randomized to their respective treatment (www.randomizer.org).

Animals were housed in standard caging of 1-5 animals/cage under 12-hour light/dark cycle controlled via automatic timer with a humidity of 30-70%. Temperature was kept within the range of 64-79° F. (18-26° C.). Autoclaved rodent chow food was provided ad libitum. Water was accessible to all animals ad libitum via individual placed water bottles in each cage. At a minimum, water bottles were replaced once per week during weekly cage changes. The water supply was drawn from the City of Philadelphia and purified using a Getinge water purifier. Water quality is tested by ULAR daily for chlorine levels and quarterly for pH and hardness. Nesting material (Nestlet®) was provided in each cage after each change. Animals were monitored daily by GTP staff and ULAR veterinary staff.

C. Vector and Vehicle Administration

MPS IIIA mice received $9 \times 10^8$ GC (low dose) per mouse or $9 \times 10^9$ GC (mid dose) or $9 \times 10^{10}$ GC (high dose) of vector per mouse or PBS in 5 µL into the right lateral cerebral ventricle at an average age of 14 weeks. Mice were anesthetized with Isoflurane. Each anesthetized mouse was grasped firmly by the loose skin behind the head and injected free hand anterior and lateral to the bregma with a Hamilton syringe fitted with a 27-gauge needle, which was adjusted to be inserted 3 mm deep.

D. Neurobehavioral Assessment

Rocking rotarod was performed to assess coordination and balance 4 months pi (MPS IIIA). Mice were habituated to the rotarod during 2 trials at a constant low speed (5 rpm) for 120 seconds. After 2 minutes rest, mice were placed back on the rotarod and submitted to a rocking paradigm were the rod rotates at a constant speed of 10 rpm with reversal of the rotation direction every other rotation. 3 trials were performed with intertrial rest of 2 minutes. Results were expressed as the average latency to fall from the rod; the longer the latency, the better the coordination.

E. Histology

Mice were euthanized by cardiac puncture exsanguination under ketamine/xylazine anesthesia 5.5 months post injection. Tissues were promptly collected, half was snap-frozen on dry ice (enzyme activity), and half was immersion-fixed in 10% neutral formalin and embedded in paraffin for histology. Collected tissues were brain, spinal cord, liver, and heart.

Hematoxylin & eosin (H&E) staining was performed according to standard protocols on paraffin sections. Histopathology was scored in brain and spinal cord by a board-certified veterinary Pathologist blinded to the treatment. Brain score was the cumulative sum of 3-grade severity scores of glial cell vacuolation in brain, neuronal vacuolation in cerebrum, neuronal vacuolation in brainstem, GFAP intensity score in brain, and mononuclear cell infiltration (maximum score of 15). Spinal cord score was the cumulative sum of 3-grade severity scores of neuronal vacuolation (more prominent in motor neurons), glial cell vacuolation, and GFAP intensity (maximum score of 9). Cumulative scores were analyzed by one-way Anova Kruskall Wallis test with post hoc Dunn's multiple comparison test, alpha 0.05.

Lysosomal storage was assessed by LIMP2 immunostaining and quantification. LIMP2 immunostaining was performed on 6 µm sections from formalin-fixed paraffin-embedded brain tissue. Sections were deparaffinized through an ethanol and xylene series, boiled in a microwave for 6 minutes in 10 mmol/L citrate buffer (pH 6.0) for antigen retrieval, and blocked with 1% donkey serum in PBS+0.2% Triton for 15 minutes followed by sequential incubation with primary (1 hour) and labeled secondary (45 minutes) antibodies diluted in blocking buffer. The primary antibody was rabbit anti-LIMP2 (Novus Biologicals, Littleton, Colo., 1:200) and the secondary antibody was FITC- or TRITC-labeled donkey anti-rabbit (Jackson Immunoresearch). The number of cells staining positive for LIMP2 was quantified in 2-4 brain sections from each animal (Day 90 necropsies) by trained GTP Morphology core personnel.

F. Enzyme Activity and Glycosaminoglycan Storage

For enzyme activity assays and GAGs content, proteins were extracted by mechanical homogenization (Qiagen TissueLizer) in an acidic lysis solution (0.2% triton, 0.9% NaCl, adjusted to pH 4). Samples were freeze-thawed and clarified by centrifugation. Protein was quantified by BCA assay.

SGSH activity was measured by incubating 10 µL sample with 20 µL of 5 mM 4-Methylumbelliferyl 2-Sulfamino-2-deoxy-α-D-glucopyranoside Sodium Salt (Toronto Research Chemicals) dissolved in sodium acetate 14.3 mM pH 5.5+0.7% NaCl+lead acetate 0.01M. After incubating for 17 h at 37° C., 6 µL of phosphate/citrate McIlvain buffer pH 6.7 and 10 µL of 10 U/ml alpha-glucosidase from yeast (sigma) were added to the reaction mixture and incubated overnight at 37° C. The mixture was diluted in glycine NaOH buffer, pH 10.6, and released 4-MU was quantified by fluorescence (excitation 365 nm, emission 450 nm) compared with standard dilutions of free 4-MU and normalized by the protein content.

GAGs content in tissue extract from MPS IIIA animals were measured using dye-binding method with a commercial kit used per manufacturer recommendations (Blyscan Biocolor GAGs kit).

G. Anti-Transgene Antibodies

Blood for measurement of serum anti-hSGSH antibodies was collected at several in vivo timepoints by submandibular bleeding as well as at terminal necropsy by cardiac puncture. Serum was separated and frozen on dry ice and stored at −80° C. until analyzed. Polystyrene plates were coated overnight with recombinant human SGSH (R&D Systems), 5 µg/mL in PBS, titrated to pH 5.8. Plates were washed and blocked 1 hour in 2% bovine serum albumin (BSA) in neutral PBS. Plates were then incubated with serum samples diluted 1:1000 in PBS. Bound antibody was detected with horseradish peroxidase (HRP)-conjugated goat anti-mouse antibody (Abcam) diluted 1:10,000 in PBS with 2% BSA. The assay was developed using tetramethylbenzidine substrate and stopped with 2N sulfuric acid before measuring absorbance at 450 nm.

Example 2: Determination of Minimum Effective Dose (MED) in a Murine Model of MPSIIIa Experiments were performed to evaluate the expression, bioactivity, and minimum effective dose (MED) of a single intracerebroventricular (ICV) administration of AAV9.CB7.CI.hSGSHco.rBG, an AAV9 vector expressing human SGSH, in a murine model of MPSIIIa.

AAV9.CB7.CI.hSGSH.rBG was administered through the ICV route to 3 month old MPS IIIa mice (n=10 per group) at doses of $9 \times 10^8$ GC or $9 \times 10^9$ GC or $9 \times 10^{10}$ GC (determined by ddPCR tittering of the vector) per mouse on Day 0 with a 6 month post-injection (pi) observation period. Vehicle treated MPS IIIa and heterozygous littermates served as controls (n=7-8 per group).

Bioactivity was assessed by measuring the SGSH activity at 14 days and 56 days pi in the serum and at 6 months pi in the brain, spinal cord, liver and heart. Efficacy and MED were determined by measuring performance on a rocking rotarod at 4 months pi as well as brain lysosomal storage and neuroinflammation at 6 month pi.

ICV administration of AAV9.CB7.CI.hSGSHco.rBG to MPS IIIa mice at up to $9 \times 10^{10}$ GC per mouse was well tolerated, with no treatment related clinical signs or mortality, and resulted in SGSH expression in the whole central nervous system (CNS, brain and spinal cord) as well as in peripheral tissues (liver and serum).

Figure 1B:
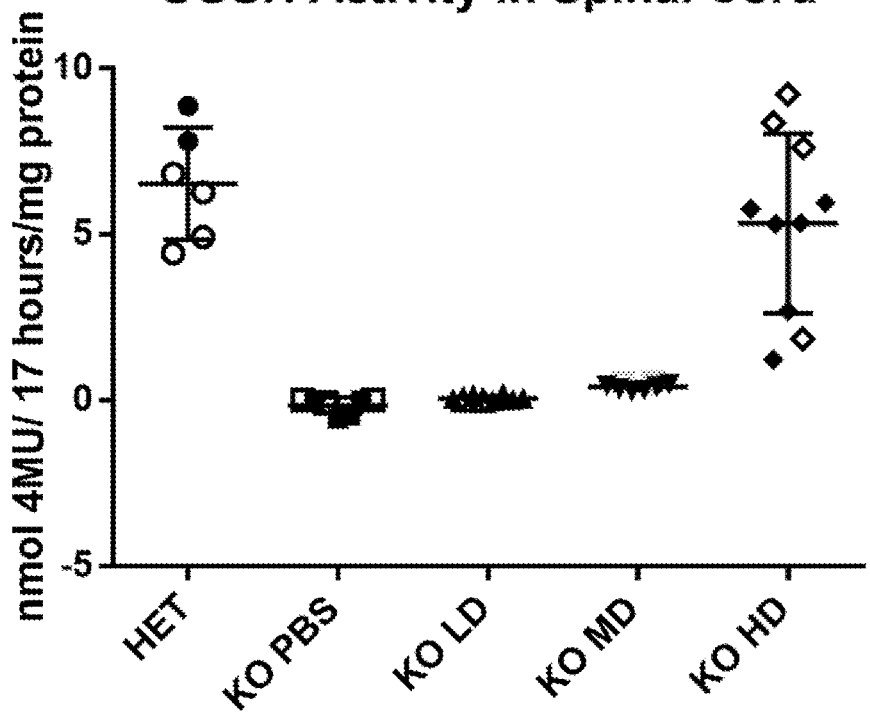
Figure 1C:
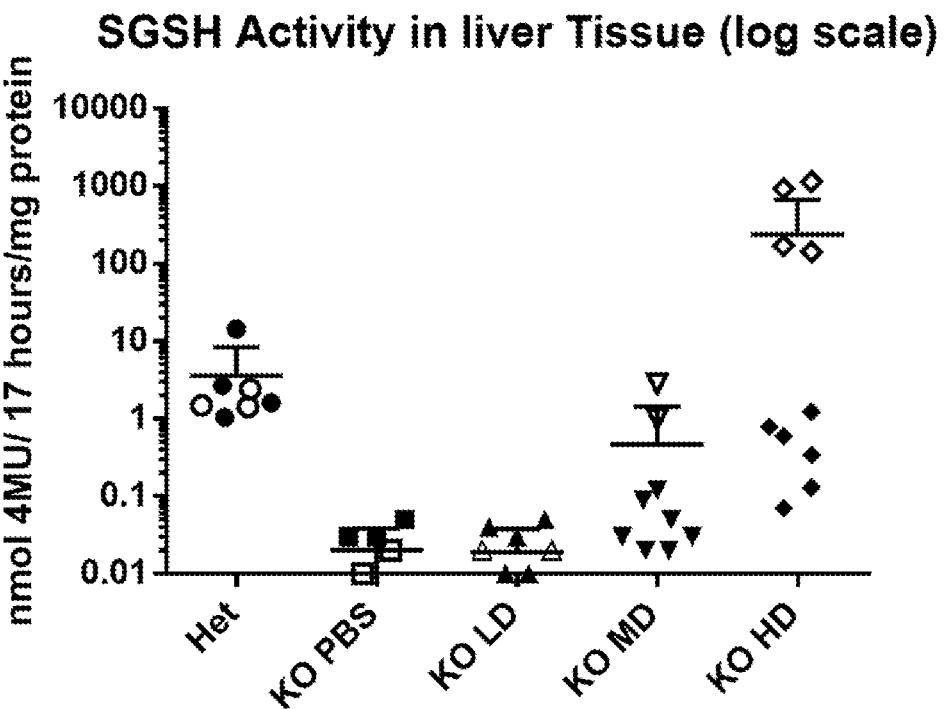
Figure 1D:
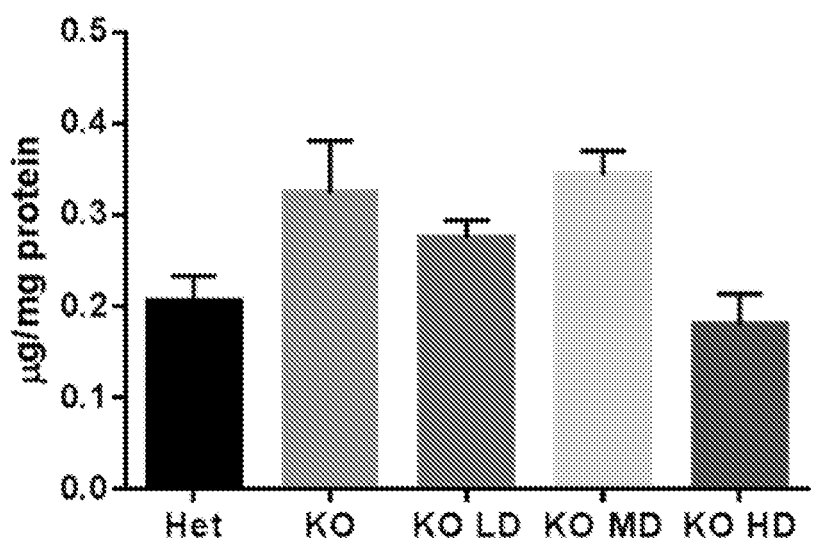
Figure 1E:
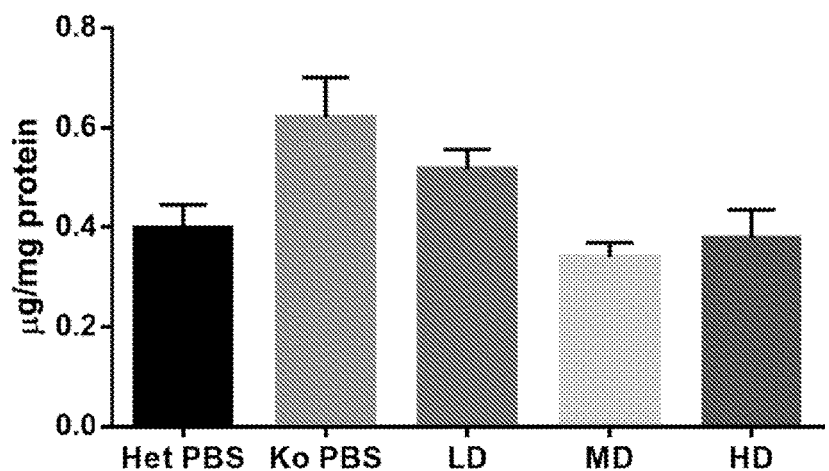
Figure 2A:
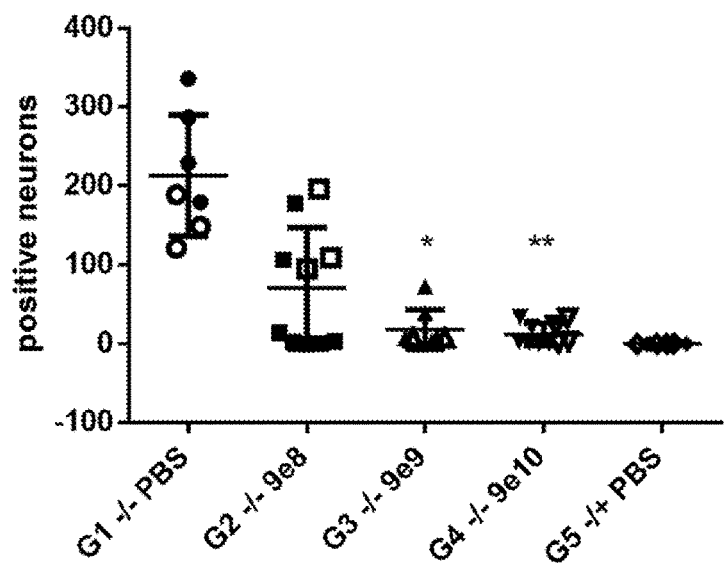
FIGS. 2A and 2B shows lysosomal storage assessed by LIMP2 immunostaining (FIG. 2B) and quantification (FIG. 2A) in brain 6 months after intracerebroventricular administration of AAV9.CB7.CI.hSGSH.rBG. LIMP2 immunostaining of lysosomal membranes showed a reduction of the storage burden at the mid dose and high dose. Open symbols represent males while solid ones represent female in FIG. 2A.
Figure 2B:
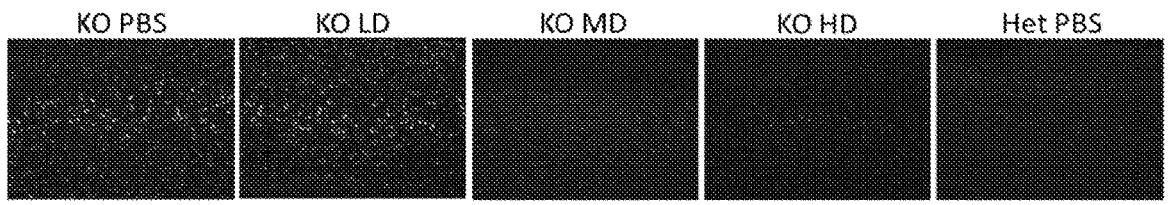
Figure 3A:
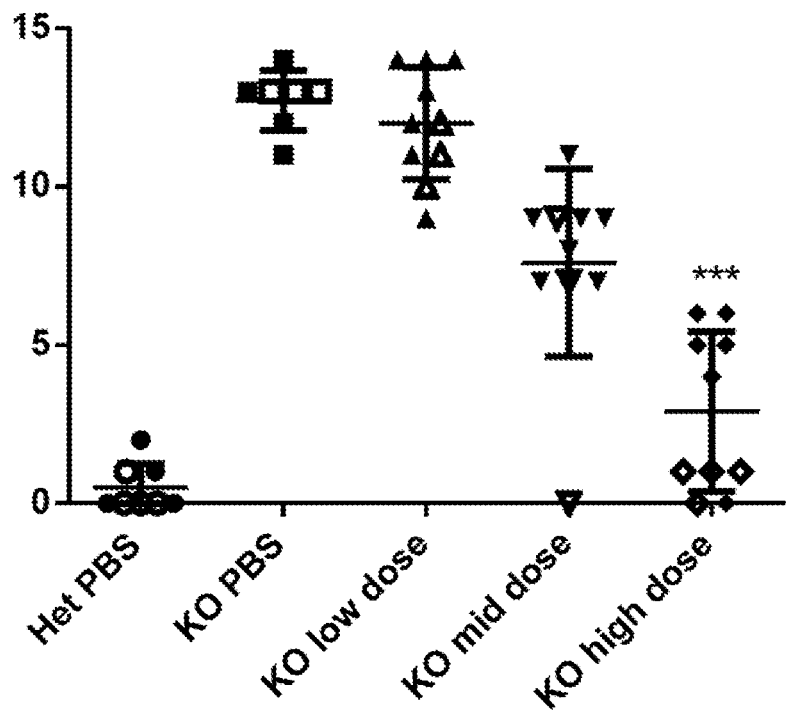
FIGS. 3A and 3B provide histopathology cumulative score in brain (FIG. 3A) and spinal cord (FIG. 3B) 6 months after ICV administration of AAV9.CB7.CI.hSGSH.rBG. Brain score is the cumulative sum of 3-grade severity scores of glial cell vacuolation in brain, neuronal vacuolation in cerebrum, neuronal vacuolation in brainstem, GFAP intensity score in brain, and mononuclear cell infiltration (maximum score of 15). Spinal cord score is the cumulative sum of 3-grade severity scores of neuronal vacuolation (more prominent in motor neurons), glial cell vacuolation, and GFAP intensity (maximum score of 9). Low dose MPS IIIa mice were similar to vehicle-treated whereas both mid dose and high dose treated mice had a decreased neuropathology score in the brain and spinal cord. The correction of neuropathology is statistically significant in the high dose group treated animals (one way Anova Kruskall Wallis test with post hoc Dunn's multiple comparison test, alpha 0.05). Open symbols represent males while solid ones represent female.
Figure 3B:
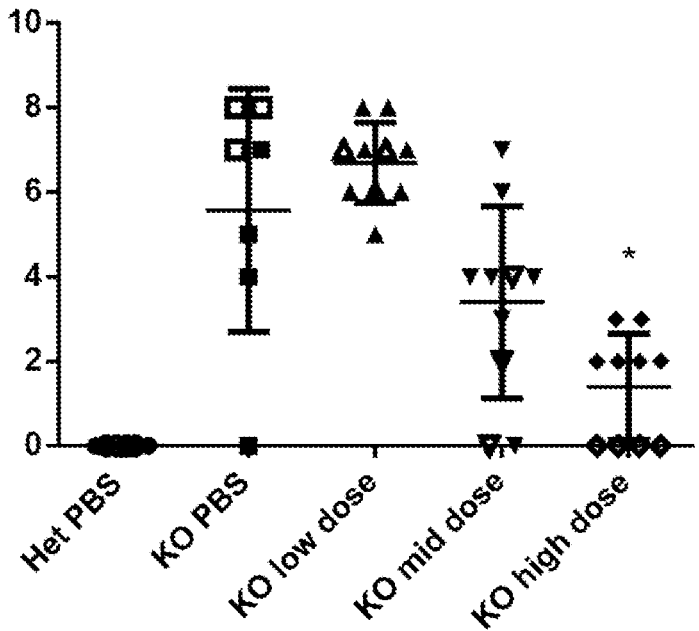
Figure 4:
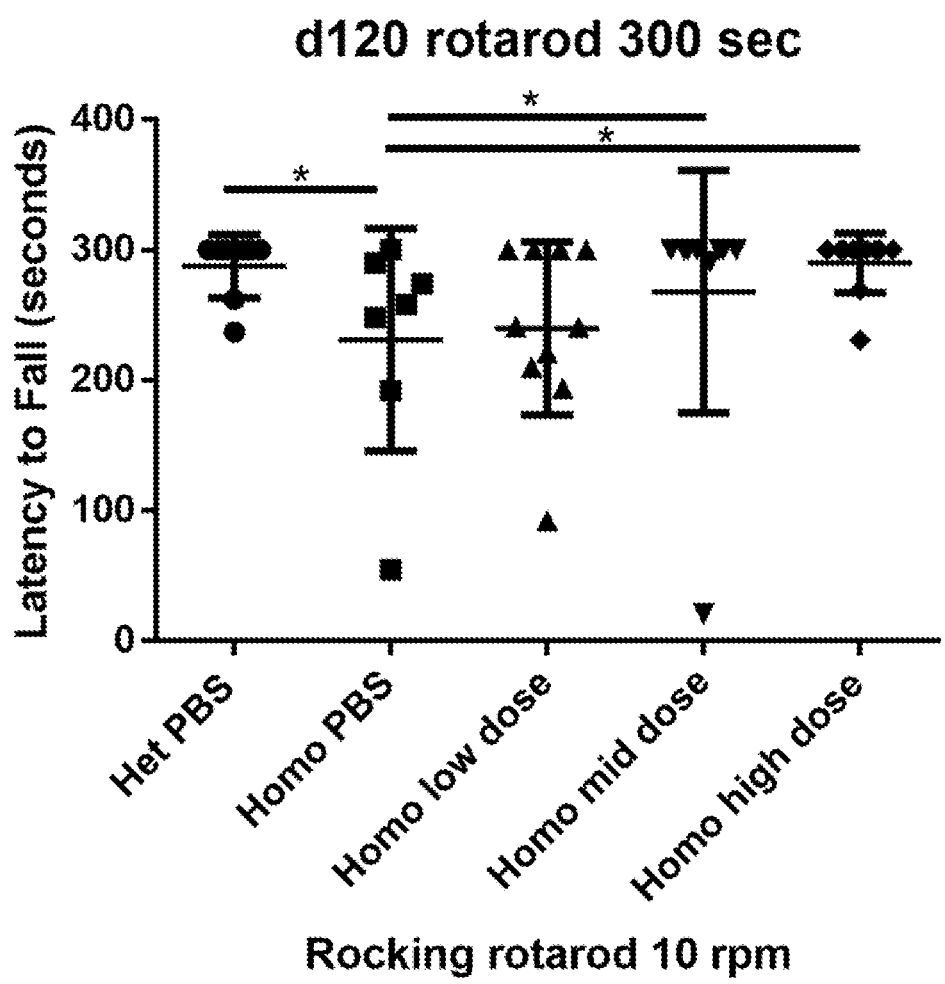
FIG. 4 provides neurologic function assessed by the rocking rotarod 6 months after ICV administration of AAV9.CB7.CI.hSGSH.rBG. Mice were positioned on a rotating rod (10 revolutions per minutes) with an inversion of the rotation direction after each revolution. The latency to fall was measured over a maximum period of 300 seconds during 3 consecutive assays. The mean latency of the 3 assays was reported as an indicator of balance and coordination. *Mann-Whitney test p<0.05. Vehicle-treated MPS IIIa mice presented a neurologic deficit that caused them to fall from the rotating rod before heterozygous mice. Both mid-dose and high-dose treated mice performed significantly better than the untreated and similarly to heterozygous mice. The low dose MPS IIIa mice however performed as vehicle-treated.

There were dose dependent increases in SGSH activity in the brain, spinal cord and liver at 6 month pi (FIGS. 1A to 1C) with enzymatic activity close to heterozygous level at the mid dose and above the heterozygous level at high dose. Total glycosaminoglycan storage was reduced at the high dose in heart (FIG. 1D) while total glycosaminoglycan storage in brain tissue is investigated. There was dose dependent normalization of the lysosomal compartment, as shown by reductions in LIMP2 staining in the brain at the mid- and high doses 6 months pi (FIGS. 2A and 2B). In haematoxylin and eosin (H&E) stained brain sections, dose dependent reductions in the amount and frequency of glial and neuronal vacuolation, indicators of lysosomal storage, were observed (FIG. 3A). GFAP immunostaining also revealed reduction of neuroinflammation at all doses in the brain and at the high dose only in spinal cord (FIG. 3B). Corresponding to the changes in CNS lysosomal content and improvements in disease-related morphology in the H&E stained sections, there were improvements in the balance and coordination assessed by the rocking rotarod assay at 4 month pi with statistically significant improvement at the mid dose and high dose (FIG. 4).

The test article and injection procedure were well tolerated. No clinical abnormality was noted in the mice apart from the MPS IIIa phenotype related signs. All but one mouse survived up to the scheduled euthanasia. The mouse that died was a mid dose treated MPS IIIa male that had to be euthanized 4 days after the ICV injection due to severe fighting wounds. This was related to cage mate aggression and not treatment or procedure related. There was no evidence of test-article related toxicity in the brain on histopathology, although changes related to the ICV administration procedure itself were observed in some mice (hemosiderophages and mononuclear cell infiltrates in the periventricular parenchyma and meninges).

In conclusion, AAV9.CB7.CI.hSGSH.rBG was well tolerated in MPS IIIa mice at all dose levels and resulted in dose-dependent increases in SGSH levels (expression and enzymatic activity) that were associated with improvements in both CNS and peripheral parameters of MPS IIIa with correction of the neurobehavioral phenotype. The middle dose administered, $9 \times 10^9$ GC, was the minimum effective dose in this study.

Example 3: Long Term Effects of AAV.hSGSH Administration

Experiments were performed to investigate the long-term effects of AAV.hSGSH on MPS IIIa mice. Twenty MPS IIIa mice received a high dose of AAV9.CB7.CI.hSGSH.rBG ($9 \times 10^{10}$ GC, ICV) at 2 months of age. An additional twenty MPS IIIa mice and twenty wild-type mice were received PBS control injections. The mice were monitored for 7 months post injection, during which they were assigned clinical scores weekly and underwent behavioral and cognitive testing.

A multiparameter grading scale was developed to evaluate disease correction and response to treatment for the duration of the study. Mice were assigned a score based on an assessment of a combination of tremor, posture, fur quality, clasping, corneal clouding, and gait/mobility (FIG. 5). The clinical scoring system was adapted based on previously described methods (see, e.g., Burkholder et al. Curr Protoc Mouse Biol. June 2012, 2:145-65; Tumpey et al. J Virol. May 1998, 3705-10; and Guyenet et al. J Vis Exp, May 2010, 39; 1787). Clinical scores were improved for both male (FIG. 6A) and female (FIG. 6B) MPS IIIa mice that were administered AAV.hSGSH.

Figure 7:
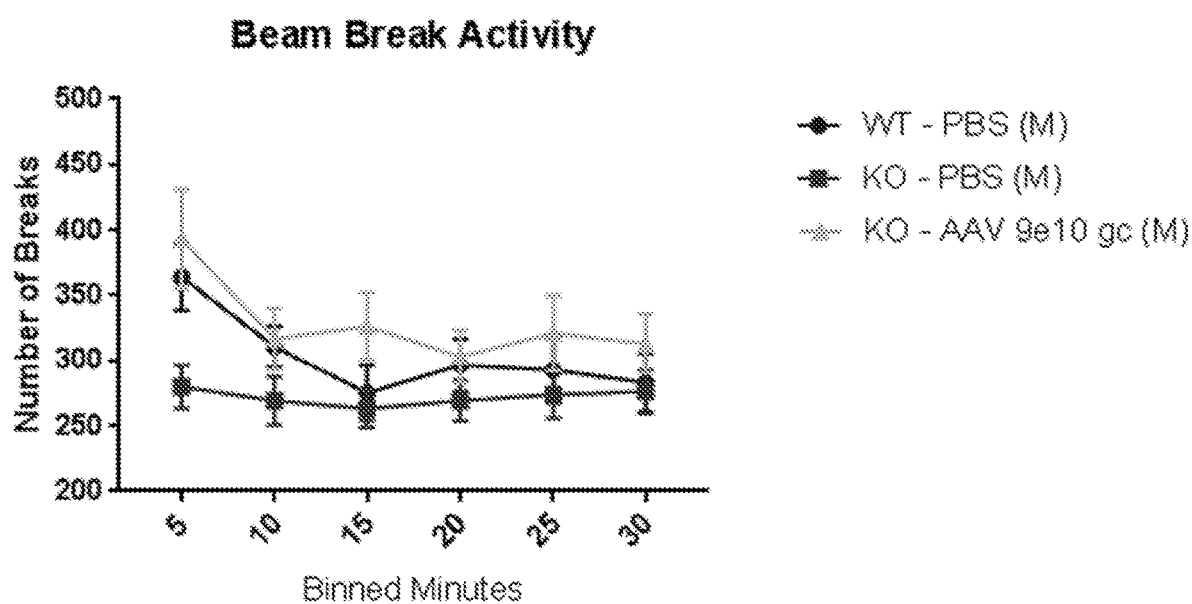
FIG. 7 provides results from measurements of open field movement (as assessed by beam break activity) following high-dose administration of AAV9.CB7.CI.hSGSH.rBG to MPS IIIa (KO) mice. Control groups of wildtype (WT) and MPS IIIa (KO) mice that received PBS injections were also evaluated.
Figure 8A:
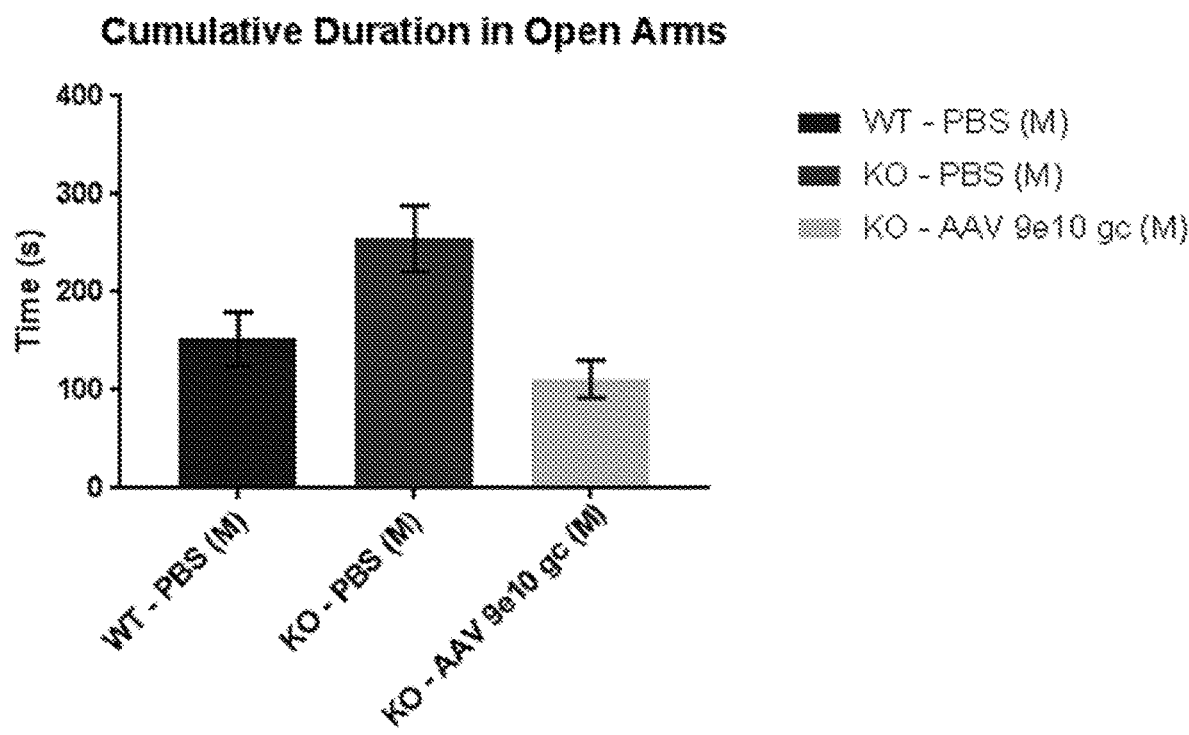
FIGS. 8A and 8B provide results from an elevated maze assays performed with MPS IIIa mice that received a high-dose of AAV9.CB7.CI.hSGSH.rBG. Open arm activity was measured in terms of duration (FIG. 8A) and frequency (FIG. 8B). Control groups of wildtype (WT) and MPS IIIa (KO) mice that received PBS injections were also evaluated.
Figure 8B:
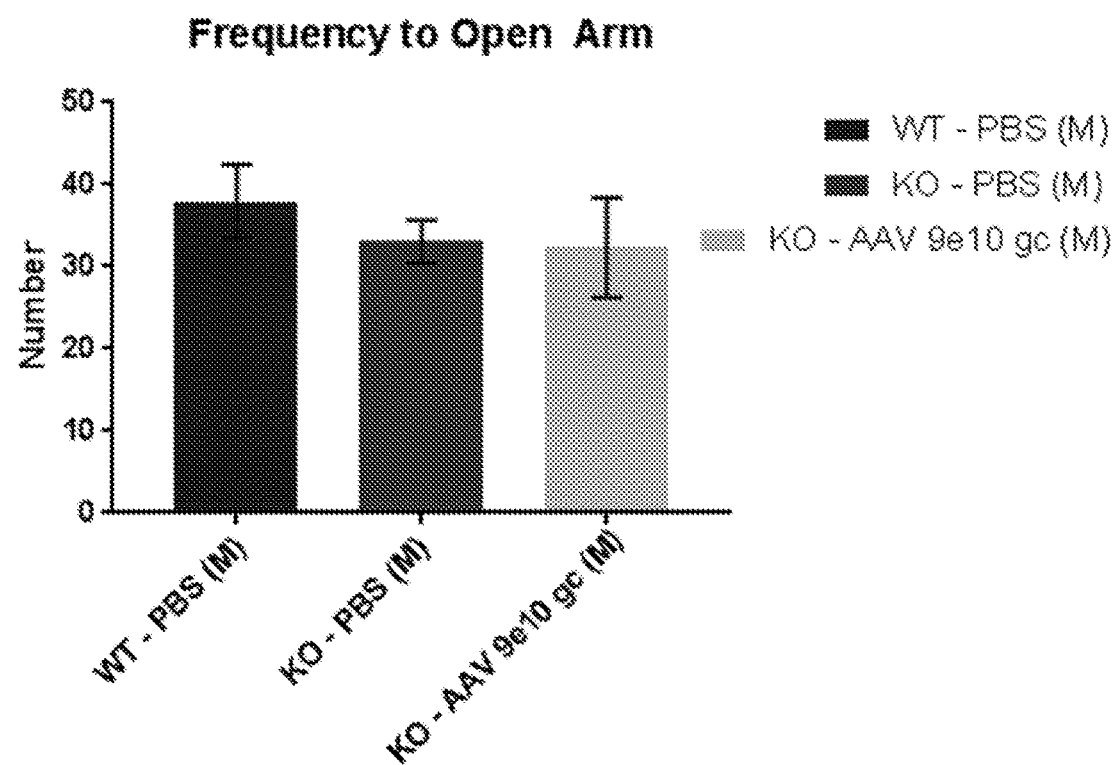

Cognitive improvement and anxiety correction of MPS IIIa mice in the study were evaluated by assessing movement in an open field (i.e. beam break measurement as described, e.g., in Tatem et al. J Vis Exp, 2014, (91):51785) and the elevated plus maze assay (as described, e.g., in Walf and Frye, Nat Protoc, 2007, 2(2): 322-328. Results from the beam break assay indicated that MPS IIIa mice that were administered AAV.hSGSH had activity levels comparable to control mice after 30 minutes (FIG. 7). Results of the elevated maze testing indicated decreased sensitivity/anxiety to fear induced by open space and height in MPS IIIa mice that received AAV.hSGSH (FIG. 8A). Further, measurement of frequency of entries to open arms suggest that the MPS IIIa mice that were administered AAV.hSGSH had intact curiosity to explore and motricity (FIG. 8B).

After neurobehavior testing, mice are euthanized and their organs are sampled to investigate enzymatic activity and lysosomal storage correction in the brain.

Overall, the results from these long-term studies suggest that AAV.hSGSH treatment can improve health and restore normal cognitive behavior in MPS IIIa mice.

Example 4: Pharmacology/Toxicology Study in Rhesus Macaque

Experiments are performed to evaluate the safety of intrathecal administration of two doses of AAV.hSGSH and the effect of peri-immunosuppression.

Control article is administered via suboccipital puncture to 2 macaques (1 male and 1 female) in Group 1. Test Article (AAV.hSGSH) is administered via suboccipital puncture to 12 rhesus macaques randomized to Groups 2-5. Macaques in Group 2 receive AAV.hSGSH at high dose (N=3); macaques in Group 3 receive AAV.hSGSH at low dose (N=3); and macaques in Groups 4 and 5 are placed on an immunosuppression regimen and receive high dose or low dose of AAV.hSGSH, respectively (N=3/group). Blood and cerebrospinal fluid are collected as part of a general safety panel. Serum and peripheral blood mononuclear cell (PBMC) are collected to investigate humoral and cellular immune response to the capsid and transgene.

Following completion of the in-life phase of these studies at 90±3 days post-vector administration, macaques are necropsied with tissues harvested for a comprehensive histopathological examination. Lymphocytes are harvested from spleen, and bone marrow to examine the presence of CTLs in these organs at the time of necropsy.

(Sequence Listing Free Text)
The following information is provided for sequences containing free text under numeric identifier <223>.

| SEQ ID NO: (containing free text) | Free text under <223> |
|---|---|
| 1 | <223> Engineered nucleic acid sequence encoding human N-sulfoglycosamine sulfohydrolase (hSGSH) |
| 4 | <223> rAAV vector genome AAV.CB7.CI.hSGSHco.rBG |
|  | <220> |
|  | <221> repeat_region |
|  | <222> (1) . . . (130) |
|  | <223> AAV2 5'ITR |
|  | <220> |
|  | <221> promoter |
|  | <222> (198) . . . (579) |
|  | <223> CMV IE promoter |
|  | <220> |
|  | <221> promoter |
|  | <222> (582) . . . (863) |
|  | <223> CB promoter |
|  | <220> |
|  | <221> TATA_signal |
|  | <222> (836) . . . (839) |
|  | <220> |
|  | <221> Intron |
|  | <222> (958) . . . (1930) |
|  | <223> chicken beta-actin |

(Sequence Listing Free Text)
The following information is provided for sequences containing free text under numeric identifier <223>.

| SEQ ID NO: (containing free text) | Free text under <223> |
|---|---|
|  | <220> |
|  | <221> CDS |
|  | <222> (1948) . . . (3459) |
|  | <223> Engineered nucleic acid sequence encoding human N-sulfoglycosamine sulfohydrolase (hSGSH) |
|  | <220> |
|  | <221> polyA_signal |
|  | <222> (3493) . . . (3619) |
|  | <223> Rabbit globin poly A (rBG, RBG) |
|  | <220> |
|  | <221> repeat_region |
|  | <222> (3708) . . . (3837) |
|  | <223> AAV2 3'ITR |
| 5 | <223> Synthetic Construct |
| 6 | <223> capsid protein VP1 of adeno-associated virus 9 |
| 7 | <223> nucleic acid sequence encoding capsid protein VP1 of adeno-associated virus 9 |

All publications cited in this specification are incorporated herein by reference in their entireties, as is U.S. Provisional Patent Application No. 62/593,081, filed Nov. 30, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant AAV (rAAV) comprising an AAV capsid and a vector genome packaged therein, wherein the vector genome comprises an AAV 5' inverted terminal repeat (ITR), an engineered nucleic acid sequence encoding a functional human N-sulfoglycosamine sulfohydrolase (hSGSH), a regulatory sequence which directs expression of the hSGSH in a target cell, and an AAV 3' ITR, wherein the hSGSH coding sequence is at least 95% identical to SEQ ID NO: 1.

2. The rAAV according to claim 1, wherein the hSGSH coding sequence is SEQ ID NO:1.

3. The rAAV according to claim 1, wherein the regulatory sequence comprises a promoter.

4. The rAAV according to claim 1, wherein the regulatory sequence comprises an enhancer.

5. The rAAV according to claim 1, wherein the regulatory sequence comprises an intron.

6. The rAAV according to claim 1, wherein the regulatory sequence comprises a poly A.

7. The rAAV according to claim 1, wherein the AAV vector genome comprises the sequence of SEQ ID NO: 4 (AAV.CB7.CI.hSGSHco.RBG).

8. The rAAV according to claim 1, wherein the AAV capsid is an AAV9 capsid.

9. A composition comprising a rAAV according to claim 1 in a formulation buffer.

10. The composition according to claim 9, which is suitable for co administration with a functional hSGSH protein or a functional Sulfatase-modifying factor 1 (SUMF1).

11. The composition according to claim 9, which is formulated for delivery via intracerebroventricular (ICV), intrathecal (IT), intracisternal or intravenous (IV) injection.

12. The composition according to claim 9, which is administrable at a dose $1 \times 10^9$ GC per gram of brain mass to about $1 \times 10^{13}$ GC per gram of brain mass.

13. The composition according to claim 9, which is formulated to have a pH of about 7.28 to about 7.32.

14. A method of treating a human subject diagnosed with MPS IIIA and/or improving gait or mobility, reducing tremors, reducing spasms, improving posture, or reducing the progression of vision loss in a subject in need thereof, comprising administering to the subject a suspension of a rAAV according to claim 1 in a formulation buffer at a dose of $1 \times 10^9$ GC per gram of brain mass to about $1 \times 10^{13}$ GC per gram of brain mass.

15. The method according to claim 14, wherein the suspension comprises at least $1 \times 10^9$ genome copies (GC)/mL of the rAAV.

16. The method according to claim 14, wherein the suspension is suitable for co-administration with a functional hSGSH protein or a functional SUMF1 protein.

17. The method according to claim 14, wherein the suspension is delivered into the subject intracerebroventricularly, intrathecally, or intravenously.

18. The method according to claim 14, wherein the suspension has a pH of about 7.28 to about 7.32.

19. The method according to claim 14, wherein
(a) the subject receives an enzyme replacement therapy at a decreased dosage or with a lower frequency compared to a standard treatment via the enzyme replacement therapy only; and/or
(b) the subject demonstrates an improvement of biomarkers related to MPS IIIA.

20. The method according to claim 14, wherein the rAAV is administered more than once to the subject.

21. A vector comprising an engineered nucleic acid sequence encoding a functional hSGSH and a regulatory sequence which directs expression thereof in a target cell, wherein the hSGSH coding sequence is at least 96% identical to SEQ ID NO: 1.

22. The vector according to claim 21, wherein the hSGSH coding sequence is SEQ ID NO: 1.

23. The vector according to claim 21, which is a recombinant virus, a plasmid, Lipoplexes, a Polymersome, Polyplexes, a dendrimer, a cell penetrating peptide (CPP) conjugate, a magnetic particle, or a nanoparticle.

24. The vector according to claim 21, which is an adeno-associated virus (AAV), an adenovirus, a bocavirus, a hybrid AAV/bocavirus, a herpes simplex virus, or a lentivirus.

25. The vector according to claim 21, wherein the target cell is an isolated cell, a cultured cell, a cell line, an *Escherichia coli* cell, a yeast cell, a human cell, a non-human cell, a mammalian cell, a non-mammalian cell, an insect cell, an HEK-293 cell, a liver cell, a kidney cell, a cell of the central nervous system, a neuron, a glial cell, or a stem cell.

* * * * *